(12) United States Patent
Yamano et al.

(10) Patent No.: US 8,373,007 B2
(45) Date of Patent: Feb. 12, 2013

(54) STABLE VINAMIDINIUM SALT AND NITROGEN-CONTAINING HETEROCYCLIC RING SYNTHESIS USING THE SAME

(75) Inventors: Mitsuhisa Yamano, Osaka (JP); Yasuhiro Sawai, Osaka (JP); Masahiro Mizuno, Osaka (JP)

(73) Assignee: Takeda Pharmaceutical Company Ltd., Osaka-Shi (JP)

( * ) Notice: Subject to any disclaimer, the term of this patent is extended or adjusted under 35 U.S.C. 154(b) by 239 days.

(21) Appl. No.: 12/934,801

(22) PCT Filed: Mar. 27, 2009

(86) PCT No.: PCT/JP2009/056315
§ 371 (c)(1),
(2), (4) Date: Sep. 27, 2010

(87) PCT Pub. No.: WO2009/119817
PCT Pub. Date: Oct. 1, 2009

(65) Prior Publication Data
US 2011/0015399 A1    Jan. 20, 2011

(30) Foreign Application Priority Data

Mar. 28, 2008  (JP) ................. 2008-087305

(51) Int. Cl.
C07C 251/00 (2006.01)
C07C 211/62 (2006.01)
C07C 211/63 (2006.01)
(52) U.S. Cl. ......... 564/248; 564/278; 564/279; 564/295
(58) Field of Classification Search .................. 564/248, 564/278, 279, 295
See application file for complete search history.

(56) References Cited

U.S. PATENT DOCUMENTS

| 3,288,784 | A | * | 11/1966 | Speziale et al. ............... 540/609 |
| 4,774,020 | A | | 9/1988 | Kitano et al. |
| 4,788,335 | A | * | 11/1988 | Wagner et al. ................ 564/279 |
| 4,857,663 | A | * | 8/1989 | Wagner et al. ................ 564/279 |
| 2002/0042516 | A1 | | 4/2002 | Tom et al. |
| 2002/0065291 | A1 | | 5/2002 | Humphrey et al. |
| 2002/0132806 | A1 | | 9/2002 | Ruggeri et al. |
| 2002/0187988 | A1 | | 12/2002 | Sturr et al. |

FOREIGN PATENT DOCUMENTS

| JP | 62-10083 A | 8/1994 |
| JP | 2001-139555 A | 5/2001 |
| JP | 2004-510738 T | 4/2004 |
| JP | 2004-510766 T | 4/2004 |
| WO | WO-02/22616 A2 | 3/2002 |
| WO | WO-02/28395 A1 | 4/2002 |
| WO | WO-02/28840 A1 | 4/2002 |

OTHER PUBLICATIONS

Perez-Mayoral, Dalton Treans., 2012, vol. 41, 4036, www.rcs.org/dalton.*

Bergman, et. al., Cyclization of N-Acylanthranilic Acids With Vilsmeier Reagents, Chemical and Structural Studies, *Tetrahedron*, 1996, 52(3) p. 753-770.
Tom et al, An Efficient Synthesis of Substituted Quinolines, *Synthesis*, 2001, No. 9, p. 1351-1355.
Ragan et al, Shock Sensitivity of a Vinamidinium Bis-Perchlorate Reagent and Demonstration of a Lower Energy Alternative, *Synlett*, 2000, No. 8, p. 1172-1174.
Gompper et al, An Access to Unsymmetrically Substituted Dibenzo[14]Annulen Es, *Tetrahedron Letters*, 1992, 33(28), p. 3989-3992.
Gupton et al., Application of 2-Substituted Vinamidinium Salts to the Synthesis of 2,4-Disubstituted Pyrroles, *The Journal of Organic Chemistry*, 1990, 55(15), p. 4735-4740.
Angus et al, Efficient Synthesis of 4-Acylisoxazole Derivatives From Triformylmethane, *Synthesis*, 1988, p. 746-748.
Davies et al., A Practical Synthesis of a COX-2-Specific Inhibitor, *The Journal of Organic Chemistry*, 2000, 65, p. 8415-8420.
Ragan et al, Perchloric Acid Salts, *Chemical & Engineering News*, 2000, 78(10), p. 8.
Davies et al., A[2+2] Cycloaddition Route to Dimethylaminomethylene Vinamidinium Salts, *Organic Letters*, 2002, 4(17), p. 2969-2972.
Davies et al., Demonstrating the Synergy of Synthetic, Mechanistic, and Computational Studies in a Regioselective Aniline Synthesis, *The Journal of Organic Chemistry*, 2004, 69, p. 1298-1308.
Marcoux et al., A General Preparation of Pyridines and Pyridones Via the Annulation of Ketones and Esters, *The Journal of Organic Chemistry*, 2001, 66, p. 4194-4199.

(Continued)

*Primary Examiner* — Brian J Davis
(74) *Attorney, Agent, or Firm* — Edwards Wildman Palmer LLP; David G. Conlin; Lisa Swiszcz

(57) ABSTRACT

Disclosed is a vinamidinium salt represented by the formula (I):

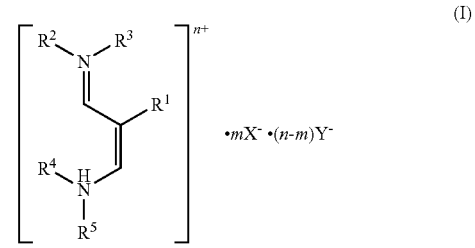

[wherein $R^1$ represents a hydrogen atom, a halogen atom, an optionally substituted hydrocarbon group or the like; $R^2$ and $R^3$ are the same or different and each represents a lower alkyl group, or alternatively $R^2$ and $R^3$ may combine together to form a ring; $R^4$ and $R^5$ are the same or different and each represents a lower alkyl group, or alternatively $R^4$ and $R^5$ may combine together to form a ring; X and Y are the same or different and each represents a bromine atom or a chlorine atom; n represents a number of not less than 2; and m represents 0 or n], and methods for synthesizing a heterocyclic ring compound using the salt.

11 Claims, No Drawings

OTHER PUBLICATIONS

Marcoux et al., Annulation of Ketones With Vinamidinium Hexafluorophosphate Salts: An Efficient Preparation of Trisubstituted Pyridines, *Organic Letters*, 2000, 2(15), p. 2339-2341.

Davies et al, An Efficient Preparation of Vinamidinium Hexafluorophosphate Salts, *The Journal of Organic Chemistry*, 2000, 65, p. 4571-4574.

Davies et al, Preparation and Novel Reduction Reactions of Vinamidinium Salts, *The Journal of Organic Chemistry*, 2001, 66, p. 251-255.

Niedrich et al., Untersuchungen Zur Synthese Von 3-Amino-5-(Pyrid-4-YL)- 1,2-Dihydro-Pyrid-2-On (Cordemcura®) Aus Technischen Pyridinbasegemischen, *Die Pharmazie*, 1986, 41(3), p. 173-175.

Gaillard, S. et al., Preparation of 1,4-Dihydroquinolines Bearing a Chiral Sulfoxide Group: New Highly Enantioselective Recyclable NADH Mimics, Synlett, 2005, No. 3, pp. 441-444.

Krasnaya, A. et al., Synthesis and Valance Isomerization of δ-dimethylamino-γ-chlorodienones to 2-dimethylamino-3-chloro-2H-pyrans $^1$H and $^{13}$C NMR and UV Spectroscopic Study, Russian Chemical Bulletin, 1985, vol. 34, No. 5, pp. 978-994.

Malleron, J., et al., Penta-and Hexadienoic Acid Derivatives: A Novel Series of 5-Lipoxygenase Inhibitors, J. Med. Chem., 1990, vol. 33, pp. 2744-2749.

Reichardt C., et al, Darstellung and Reaktionen von-2(Dialkylamino)malon-aldehyden, Liebigs Ann. Chem, 1982, pp. 530-535.

Wypych, JC et al., Reaction of Aldimine Anions with Vinamidinium Chloride: Three Component Access to 3-Alkylpyridines and 3-Alkylpyridinium Salts and Access to 2-Alkyl Glutaconaldehyde Derivatives, Journal of Organic Chemistry, 2008, vol. 73, pp. 1169-1172.

Supplementary European Search Report for corresponding European Patent Application No. 09723915.6 (Oct. 5, 2011).

* cited by examiner

STABLE VINAMIDINIUM SALT AND NITROGEN-CONTAINING HETEROCYCLIC RING SYNTHESIS USING THE SAME

TECHNICAL FIELD

The present invention relates to a stable vinamidinium salt, crystals thereof, an acetic acid solution thereof, and a method for synthesizing a nitrogen-containing heterocyclic ring using them.

BACKGROUND ART

In the construction of an aromatic ring such as a benzene ring, a quinoline ring, a pyridine ring, a pyrrole ring, a pyrazole ring, or a pyrimidine ring having substituent(s), a method utilizing a vinamidinium salt has been known and, currently, its usefulness has been reevaluated in many reports (see, e.g. Patent Documents 1-3 and non-Patent Documents 1-6, and 9). Among them, the method is carried out industrially as a pyridine ring construction reaction in a synthesis step of Etoricoxib which is a COX-2 inhibitor (see, non-Patent Document 6).

However, when using the vinamidinium salt industrially, there is a difficult point that isolated crystals thereof have hygroscopicity and therefore, cause degradation by deliquescing. Crystals of a halogen anion salt having a counteranion such as Cl$^-$ are said to have particularly strong hygroscopicity and therefore, it is problematic to deal with the crystals by isolating them in a larger scale production (see, non-Patent Document 12).

Then, it seems that crystals known from old, for example, crystals of ClO$_4^-$ salt were used at first. However, as a result of safety evaluation, it has become apparent that the crystals have significantly explosive properties (see, non-Patent Document 7) and therefore, a BF$_4^-$ salt is now used (see, Patent Document 2). However, there is a problem that the BF$_4^-$ salt corrodes a glass container in case of carrying out a heating reaction.

Meanwhile, currently, a PF$_6^-$ salt has newly been isolated and the use thereof has been reported (see, non-Patent Documents 6, and 8-13), but there is a drawback that the PF$_6^-$ salt is more expensive than other salts.

Patent Document 1: JP-A-62-10083
Patent Document 2: JP-A-2001-139555
Patent Document 3: WO 2002/28840
non-Patent Document 1: Synthesis, (2001), (9), 1351-1355
non-Patent Document 2: Synlett, (2000), (8), 1172-1174
non-Patent Document 3: Tetrahedron Letters, (1992), 33(28), 3989-3992
non-Patent Document 4: The Journal of Organic Chemistry, (1990), 55(15), 4735-4740
non-Patent Document 5: Synthesis, (1988), 746-748
non-Patent Document 6: The Journal of Organic Chemistry, (2000), 65, 8415-8420
non-Patent Document 7: Chemical & Engineering News, (2000), 78(10), 8
non-Patent Document 8: Organic Letters, (2002), 4(17), 2969-2972
non-Patent Document 9: The Journal of Organic Chemistry, (2004), 69, 1298-1308
non-Patent Document 10: The Journal of Organic Chemistry, (2001), 66, 4194-4199
non-Patent Document 11: Organic Letters, (2000), 2(15), 2339-2341
non-Patent Document 12: The Journal of Organic Chemistry, (2000), 65, 4571-4574
non-Patent Document 13: The Journal of Organic Chemistry, (2001), 66, 251-255

DISCLOSURE OF THE INVENTION

Problem To Be Solved By The Invention

Objectives of the present invention are to provide a vinamidinium salt which can be used as a universal reagent useful for the synthesis of various nitrogen-containing heterocyclic aromatic rings having substituent(s), has excellent storage stability and reaction selectivity, is free from corrosivity to glass, and can be produced inexpensively; an acetic acid solution thereof; and a process for constructing a nitrogen-containing heterocyclic aromatic ring such as a quinoline ring, a pyridine ring, a pyrrole ring, a pyrazole ring, or a pyrimidine ring using them.

Means For Solving The Problem

With respect to a method for synthesizing a compound having a substituted quinoline skeleton as a candidate compound for medicine, the present inventors have studied the construction of a quinoline skeleton using a vinamidinium salt intensively and have found that most excellent reaction selectivity can be obtained when using the salt having Cl$^-$ as a counteranion. They have further studied intensively and have succeeded in obtaining crystals of a vinamidinium salt having a halogen anion, whose valency number has not ever been known, in the stable form. In addition to this, they have found that an acetic acid solution of the vinamidinium salt having a halogen anion has excellent storage stability. Thus the present invention has been completed.

That is, the present invention provides:
(1) A compound represented by the formula (I):

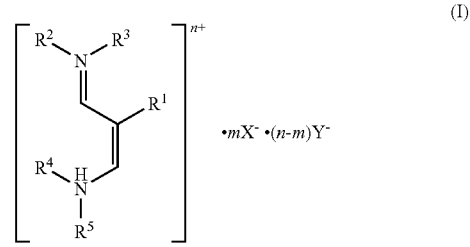

wherein R$^1$ represents a hydrogen atom, a halogen atom, a nitro group, a nitroso group, a cyano group, an optionally substituted hydrocarbon group, an optionally substituted heterocyclic group, an optionally substituted hydroxy group, an optionally substituted amino group, an optionally substituted mercapto group, an optionally substituted acyl group, an optionally substituted carbamoyl group, or an optionally substituted sulfonyl group, R$^2$ and R$^3$ are the same or different and each represents a lower alkyl group, or R$^2$ and R$^3$ may combine together to form a ring, R$^4$ and R$^5$ are the same or different and each represents a lower alkyl group, or R$^4$ and R$^5$ may combine together to form a ring, X and Y are the same or different and each represents a bromine atom or a chlorine atom, n represents a number of 2 or more, and m represents 0 to n;

(2) The compound according to the above (1), wherein R$^1$ is a halogen atom, a lower alkyl group substituted by N,N-di-lower alkyl-imino group, or a C$_6$-C$_{14}$ aryl group;

(3) The compound according to the above (1), wherein R$^1$ is a lower alkyl group substituted by N,N-di-lower alkyl-imino group;

(4) The compound according to the above (1), wherein R$^1$ is a dimethyliminomethyl group;

(5) The compound according to the above (1), wherein each of $R^2$, $R^3$, $R^4$, and $R^5$ is a lower alkyl group;
(6) The compound according to the above (1), wherein n is 2 or 3;
(7) The compound according to the above (1) to (6), the following (9) or (10), wherein X and Y are a chlorine atom;
(8) The compound according to the above (1) to (6), the following (9) or (10), wherein X and Y are a bromine atom;
(9) The compound according to the above (1), wherein $R^1$ is a dimethyliminomethyl group and each of $R^2$, $R^3$, $R^4$, and $R^5$ is a $C_1$-$C_6$ alkyl group;
(10) The compound according to the above (1), wherein $R^1$ is a dimethyliminomethyl group, each of $R^2$, $R^3$, $R^4$, and $R^5$ is a methyl group and n is 3;
(11) The compound according to the above (1) to (10), which is isolated;
(12) The compound according to the above (1) to (10), which is in a solid state;
(13) The compound according to the above (1) to (10), which is a crystalline compound;
(14) An acetic acid solution of the compound according to the above (1) to (10);
(15) A compound represented by the formula (I):

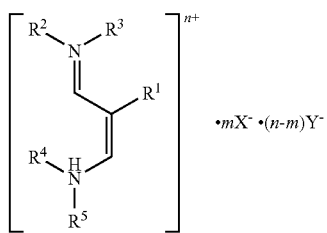

wherein $R^1$ represents a hydrogen atom, a halogen atom, a nitro group, a nitroso group, a cyano group, an optionally substituted hydrocarbon group, an optionally substituted heterocyclic group, an optionally substituted hydroxy group, an optionally substituted amino group, an optionally substituted mercapto group, an optionally substituted acyl group, an optionally substituted carbamoyl group or an optionally substituted sulfonyl group, $R^2$ and $R^3$ are the same or different and each represents a lower alkyl group, or $R^2$ and $R^3$ may combine together to form a ring, $R^4$ and $R^5$ are the same or different and each represents a lower alkyl group, or $R^4$ and $R^5$ may combine together to form a ring, X and Y are the same or different and each represents a bromine atom or a chlorine atom, n represents 3 when $R^1$ is a dimethyliminomethyl group, and otherwise n represents 2 or more; and m represents 0 to n;

(16) An acetic acid solution containing a compound represented by the formula (I'):

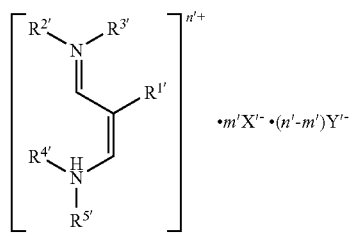

wherein $R^{1'}$ represents a hydrogen atom, a halogen atom, a nitro group, a nitroso group, a cyano group, an optionally substituted hydrocarbon group, an optionally substituted heterocyclic group, an optionally substituted hydroxy group, an optionally substituted amino group, an optionally substituted mercapto group, an optionally substituted acyl group, an optionally substituted carbamoyl group, or an optionally substituted sulfonyl group, $R^{2'}$ and $R^{3'}$ are the same or different and each represents a lower alkyl group, or $R^{2'}$ and $R^{3'}$ may combine together to form a ring, $R^{4'}$ and $R^{5'}$ are the same or different and each represents a lower alkyl group, or $R^{4'}$ and $R^{5'}$ may combine together to form a ring, $X'^-$ and $Y'^-$ are the same or different and each represents an anion, n' represents a number of 1 or more, and m' represents 0 to n';

(17) The acetic acid solution according to the above (16), wherein X' and Y' are the same or different and each represents a bromine atom or a chlorine atom;

(18) The acetic acid solution according to the above (16), wherein X' and Y' are a chlorine atom;

(19) The acetic acid solution according to the above (16), wherein X' and Y' are a bromine atom;

(20) A process for producing a compound represented by the formula (III):

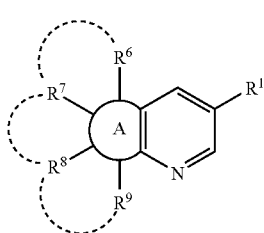

wherein ring A is as defined below, $R^1$ is the same as $R^1$ in the above (1) and $R^6$, $R^7$, $R^8$, and $R^9$ are as defined below, or a salt thereof, which comprises reacting the compound according to the above (1) with a compound represented by the formula (II):

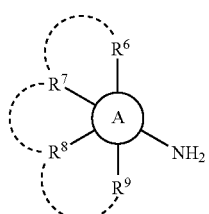

wherein ring A represents a hydrocarbon ring or a heterocyclic ring wherein the carbon atom to which the amino group in the formula (II) is attached has a double bond, $R^6$, $R^7$, $R^8$ and $R^9$ are the same or different and each represents a hydrogen atom or a substituent, or $R^6$ and $R^7$, $R^7$ and $R^8$, or $R^8$ and $R^9$ together with the adjacent atom may form a 5- to 8-membered ring;

(21) A process for producing a compound represented by the formula (III'):

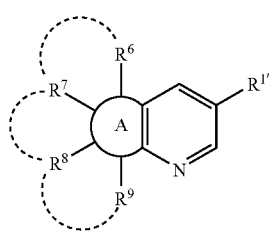

wherein ring A is as defined below, $R^{1'}$ is the same $R^{1'}$ in the above (16), and $R^6$, $R^7$, $R^8$ and $R^9$ are as defined below, or a salt thereof, which comprises reacting an acetic acid solution of the compound according to the above (16) with a compound represented by the formula (II):

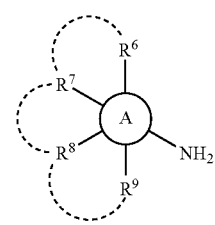

wherein ring A represents a hydrocarbon ring or a heterocyclic ring wherein the carbon atom to which the amino group in the formula (II) is attached has a double bond, $R^6$, $R^7$, $R^8$ and $R^9$ are the same or different and each represents a hydrogen atom or a substituent, or $R^6$ and $R^7$, $R^7$ and $R^8$, or $R^8$ and $R^9$ together with the adjacent atom may form a 5- to 8-membered ring;

(22) A process for producing a compound represented by the formula (V):

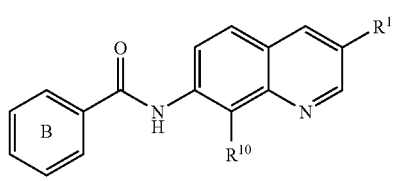

wherein $R^1$ is the same as $R^1$ in the above (1), and $R^{10}$ and ring B are as defined below, or a salt thereof, which comprises reacting the compound according to the above (1) with a compound represented by the formula (IV):

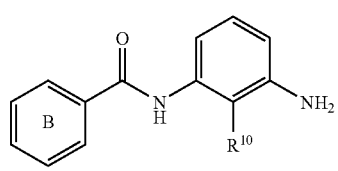

wherein $R^{10}$ represents a hydrogen atom or a substituent, and ring B represents an optionally substituted benzene ring; and

(23) A process for producing a compound represented by the formula (V'):

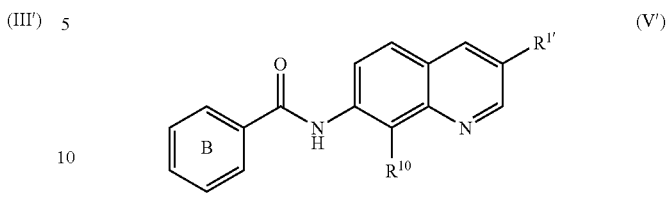

wherein $R^{1'}$ is the same as $R^{1'}$ in the above (16), and $R^{10}$ and ring B are as defined below, or a salt thereof, which comprises reacting an acetic acid solution of the compound according to the above (16) with a compound represented by the formula (IV):

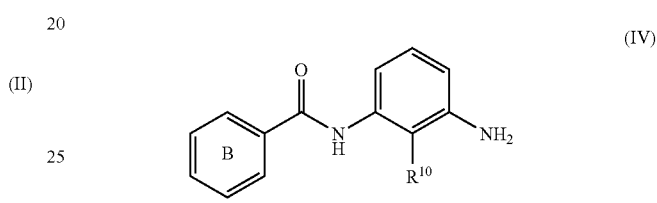

wherein $R^{10}$ and ring B are the same as $R^{10}$ and ring B in the above (22).

BEST MODE FOR CARRYING OUT THE INVENTION

In the vinamidinium salt represented by the above formula (I) or (I') of the present invention, $R^1$ and $R^{1'}$ represent a hydrogen atom, a halogen atom, a nitro group, a nitroso group, a cyano group, an optionally substituted hydrocarbon group, an optionally substituted heterocyclic group, an optionally substituted hydroxy group, an optionally substituted amino group, an optionally substituted mercapto group, an optionally substituted acyl group, an optionally substituted carbamoyl group or an optionally substituted sulfonyl group.

As used herein, the lower refers to a group having 1 to 6 of carbon atoms, preferably a group having 1 to 4 of carbon atoms.

Examples of the "halogen atom" represented by $R^1$ and $R^{1'}$ include fluorine, chlorine, bromine, and iodine.

Examples of the hydrocarbon group of the "optionally substituted hydrocarbon group" represented by $R^1$ and $R^{1'}$ include an alkyl group, an alkenyl group, an alkynyl group, a cycloalkyl group, an aryl group, and an aralkyl group.

Examples of the "alkyl group" include a $C_{1-6}$ alkyl group such as methyl, ethyl, propyl, isopropyl, butyl, isobutyl, sec-butyl, tert-butyl, pentyl, and hexyl.

Examples of the "alkenyl group" include a $C_{2-6}$ alkenyl group such as vinyl, allyl, isopropenyl, 1-butenyl, 2-butenyl, 3-butenyl, butadienyl, 2-methylallyl, hexatrienyl, and 3-octenyl.

Examples of the "alkynyl group" include a $C_{2-6}$ alkynyl group such as ethynyl, 2-propynyl, butynyl, and 3-hexynyl.

Examples of the "cycloalkyl group" include a $C_{3-6}$ cycloalkyl group such as cyclopropyl, cyclobutyl, cyclopentyl, and cyclohexyl.

Examples of the "aryl group" include a $C_{6-10}$ aryl group such as phenyl, and naphthyl.

Examples of the "aralkyl group" include a $C_{7-10}$ aralkyl group such as benzyl, and phenethyl.

Examples of the substituent(s) of the "optionally substituted hydrocarbon group" represented by $R^1$ and $R^{1'}$ include a halogen atom (e.g. fluorine, chlorine, bromine, and iodine), a nitro group, a nitroso group, a cyano group, a hydroxy group, a $C_{1-6}$ alkoxy group (e.g. methoxy, ethoxy, propoxy, isopropoxy, butoxy, isobutoxy, sec-butoxy, pentyloxy, and hexyloxy), a $C_{6-14}$ aryloxy group (e.g. phenyloxy, 1-naphthyloxy, and 2-napthyloxy), a $C_{7-16}$ aralkyloxy group (e.g. benzyloxy, and phenethyloxy), a $C_{1-6}$ alkyl-carbonyloxy group (e.g. acetoxy, and propionyloxy), a $C_{6-14}$ aryl-carbonyloxy group (e.g. benzoyloxy, and naphthylcarbonyloxy), a $C_{1-6}$ alkoxy-carbonyloxy group (e.g. methoxycarbonyloxy, ethoxycarbonyloxy, propoxycarbonyloxy, and butoxycarbonyloxy), a mono-$C_{1-6}$ alkyl-carbamoyloxy group (e.g. methylcarbamoyloxy, and ethylcarbamoyloxy), a di-$C_{1-6}$ alkyl-carbamoyloxy group (e.g. dimethylcarbamoyloxy, and diethylcarbamoyloxy), a $C_{6-14}$ aryl-carbamoyloxy group (e.g. phenylcarbamoyloxy, and naphthylcarbamoyloxy), a mercapto group, a $C_{1-6}$ alkylthio group (e.g. methylthio, ethylthio, propylthio, isopropylthio, butylthio, sec-butylthio, and tert-butylthio), a $C_{6-14}$ arylthio group (e.g. phenylthio, 1-naphthylthio, and 2-naphthylthio), a $C_{7-16}$ aralkylthio group (e.g. benzylthio, and phenethylthio), an amino group (e.g. mono-$C_{1-6}$ alkylamino group (e.g. methylamino, and ethylamino), a mono-$C_{6-14}$ arylamino group (e.g. phenylamino, 1-naphthylamino, and 2-naphthylamino), a di-$C_{1-6}$ alkylamino group (e.g. dimethylamino, diethylamino, and ethylmethylamino), a di-$C_{6-14}$ arylamino group (e.g. diphenylamino), a 5- to 7-membered saturated cyclic amino group (e.g. pyrrolidin-1-yl, piperidino, piperazin-1-yl, morpholino, thiomorpholino, and tetrahydroazepin-1-yl), a formylamino group, a $C_{1-6}$ alkyl-carbonylamino group (e.g. acetylamino), a $C_{6-14}$ aryl-carbonylamino group (e.g. benzoylamino, and naphthoylamino), a $C_{1-6}$ alkoxy-carbonylamino group (e.g. methoxycarbonylamino, ethoxycarbonylamino, propoxycarbonylamino, and butoxycarbonylamino), a $C_{1-6}$ alkyl-sulfonylamino group (e.g. methylsulfonylamino, and ethylsulfonylamino), a $C_{6-14}$ aryl-sulfonylamino group (e.g. phenylsulfonylamino, 2-naphthylsulfonylamino, and 1-naphthylsulfonylamino), a formyl group, a N,N-di-$C_{1-6}$ alkyl-imino group, a $C_{1-6}$ alkyl-carbonyl group (e.g. acetyl, propionylbutyryl, isobutyryl, valeryl, isovaleryl, and pivaloyl), a $C_{3-6}$ cycloalkyl-carbonyl group (e.g. cyclopropylcarbonyl, cyclopentylcarbonyl, and cyclohexylcarbonyl), a $C_{6-14}$ aryl-carbonyl group (e.g. benzoyl, 1-naphthoyl, and 2-naphthoyl), a $C_{7-16}$ aralkyl-carbonyl group (e.g. phenylacetyl, and 3-phenylpropionyl), a $C_{1-6}$ alkoxy-carbonyl group (e.g. methoxycarbonyl, ethoxycarbonyl, propoxycarbonyl, and tert-butoxycarbonyl), a $C_{6-14}$ aryloxy-carbonyl group (e.g. phenoxycarbonyl), a $C_{7-16}$ aralkyloxy-carbonyl group (e.g. benzyloxycarbonyl, and phenethyloxycarbonyl), a 5- to 6-membered heterocyclic carbonyl group (e.g. nicotinoyl, isonicotinoyl, furoyl, morpholinocarbonyl, thiomorpholinocarbonyl, piperazin-1-ylcarbonyl, and pyrrolidin-1-ylcarbonyl), a carbamoyl group, a mono-$C_{1-6}$ alkyl-carbamoyl group (e.g. methylcarbamoyl, and ethylcarbamoyl), a di-$C_{1-6}$ alkyl-carbamoyl group (e.g. dimethylcarbamoyl, diethylcarbamoyl, and ethylmethylcarbamoyl), a $C_{6-14}$ aryl-carbamoyl group (e.g. phenylcarbamoyl, 1-naphthylcarbamoyl, and 2-naphthylcarbamoyl), a 5- to 6-membered heterocyclic carbamoyl group (e.g. 2-pyridylcarbamoyl, 3-pyridylcarbamoyl, 4-pyridylcarbamoyl, 2-thienylcarbamoyl, and 3-thienylcarbamoyl), a $C_{1-6}$ alkyl-sulfonyl group (e.g. methylsulfonyl, and ethylsulfonyl), a $C_{6-14}$ arylsulfonyl group (e.g. phenylsulfonyl, 1-naphthylsulfonyl, and 2-naphthylsulfonyl), a $C_{7-16}$ aralkylsulfonyl group (e.g. benzylsulfonyl, and phenethylsulfonyl), a $C_{1-6}$ alkoxy-sulfonyl group (e.g. methoxysulfonyl, ethoxysulfonyl, propoxysulfonyl, and butoxysulfonyl), a $C_{6-14}$ aryloxy-sulfonyl group (e.g. phenyloxysulfonyl, 1-naphthyloxysulfonyl, and 2-naphthyloxysulfonyl), a $C_{7-16}$ aralkyloxy-sulfonyl group (e.g. benzyloxysulfonyl, and phenethyloxysulfonyl), and a 5- to 10-membered aromatic heterocyclic group (e.g. thienyl, furyl, oxazolyl, triazolyl, pyridyl, quinolyl, isoquinolyl, pyrazinyl, pyrimidinyl, pyrrolyl, imidazolyl, pyridazinyl, isothiazolyl, indolyl, benzothiazolyl, benzothienyl, and benzofuranyl). The hydrocarbon group may have 1 to 3 substituents selected from these substituents at possible positions.

The heterocyclic group of the "optionally substituted heterocyclic group" represented by $R^1$ and $R^{1'}$ represents an aromatic heterocyclic group or a non-aromatic heterocyclic group.

Examples of the "aromatic heterocyclic group" include a 5- to 6-membered aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyradinyl, and triadinyl, and a 8- to 12-membered aromatic fused heterocyclic group such as benzofuranyl, isobenzofuranyl, benzo[b]thienyl, indolyl, isoindolyl, 1H-indazolyl, benzindazolyl, benzoxazolyl, 1,2-benzoisoxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, buteridinyl, carbazolyl, α-carbolinyl, β-carbolinyl, γ-carbolinyl, acridinyl, phenoxazinyl, phenothiazinyl, phenazinyl, phenoxatiynyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazo[4,3-a]pyridyl, and 1,2,4-triazo[4,3-b]pyridazinyl.

Examples of the "non-aromatic heterocyclic group" include a 3- to 8-membered saturated or unsaturated non-aromatic heterocyclic group such as oxiranyl, azetidinyl, oxetanyl, thietanyl, pyrrolidinyl, tetrahydrofuryl, thioranyl, piperidyl, tetrahydropyranyl, morpholinyl, thiomorpholinyl, piperazinyl, 3-hexahydrocyclopenta[c]pyrrolyl, homopiperidyl, and homopiperazyl, or a non-aromatic heterocyclic group in which a part or all of the double bonds in the above-described aromatic monocyclic heterocyclic group or aromatic fused heterocyclic group are saturated such as dihydropyridyl, dihydropyrimidyl, 1,2,3,4-tetrahydroquinolyl, and 1,2,3,4-tetrahydroisoquinolyl.

Examples of the "substituent" of "an optionally substituted heterocyclic group" represented by $R^1$ and $R^{1'}$ and the number of such substituents include the same group and number as those of the above-described "optionally substituted hydrocarbon group" represented by $R^1$ and $R^{1'}$.

Examples of the substituent of "an optionally substituted hydroxy group" represented by $R^1$ and $R^{1'}$ include an optionally substituted hydrocarbon group. Examples of the "optionally substituted hydrocarbon group" include the same group as the above-described "optionally substituted hydrocarbon group" represented by $R^1$ and $R^{1'}$.

Examples of the substituent of "an optionally substituted amino group" represented by $R^1$ and $R^{1'}$ include an optionally substituted hydrocarbon group, an optionally substituted $C_{1-6}$ alkyl-carbonyl group (e.g. acetyl), an optionally substituted $C_{6-14}$ aryl-carbonyl group (e.g. benzoyl, and naphthoyl), an optionally substituted $C_{1-6}$ alkoxy-carbonyl group (e.g. methoxycarbonyl, ethoxycarbonyl, propoxycarbonyl, and butoxycarbonyl), an optionally substituted $C_{1-6}$ alkyl-sulfonyl group (e.g. methylsulfonyl, and ethylsulfonyl), an optionally substituted $C_{6-14}$ aryl-sulfonyl group (e.g. phenylsulfonyl, 2-naphthylsulfonyl, and 1-naphthylsulfonyl), and the amino group may be mono- or di-substituted by these substituents. Examples of the "optionally substituted hydrocarbon group" include the same group as the above-described "optionally substituted hydrocarbon group" represented by $R^1$ and $R^{1'}$. Examples of the substituent and the number of the substituents of "an optionally substituted $C_{1-6}$ alkyl-carbonyl group", "an optionally substituted $C_{6-14}$ aryl-carbonyl group", "an optionally substituted $C_{1-6}$ alkoxy-carbonyl group", "an optionally substituted $C_{1-6}$ alkyl-sulfonyl group" and "an optionally substituted $C_{6-14}$ aryl-sulfonyl group" include the same group and number as those of the above-described "optionally substituted hydrocarbon group" represented by $R^1$ and $R^{1'}$.

Examples of the substituent of "an optionally substituted mercapto group" represented by $R^1$ and $R^{1'}$ include an optionally substituted hydrocarbon group. Examples of the "optionally substituted hydrocarbon group" include the same group as the above-described "optionally substituted hydrocarbon group" represented by $R^1$ and $R^{1'}$.

Examples of the substituent of "an optionally substituted acyl group" represented by $R^1$ and $R^{1'}$ include an optionally substituted hydrocarbon group, and an optionally substituted hydroxy group. Examples of the "optionally substituted hydrocarbon group" include the same group as the above-described "optionally substituted hydrocarbon group" represented by $R^1$ and $R^{1'}$, and examples of the "optionally substituted hydroxy group" include the substituted hydroxy group in the above-described "optionally substituted hydroxy group" represented by $R^1$ and $R^{1'}$.

Examples of the substituent of "an optionally substituted carbamoyl group" represented by $R^1$ and $R^{1'}$ include an optionally substituted hydrocarbon group. Examples of the "optionally substituted hydrocarbon group" include the same group as the above-described "optionally substituted hydrocarbon group" represented by $R^1$ and $R^{1'}$ and the hydrocarbon group may be mono- or di-substituted by these substituents.

Examples of the substituent of "an optionally substituted sulfonyl group" represented by $R^1$ and $R^{1'}$ include an optionally substituted hydrocarbon group. Examples of the "optionally substituted hydrocarbon group" include the same group as the above-described "optionally substituted hydrocarbon group" represented by $R^1$ and $R^{1'}$.

$R^1$ and $R^{1'}$ are preferably a hydrogen atom, a halogen atom, a nitro group, a nitroso group, a cyano group, an optionally substituted hydrocarbon group, and an optionally substituted hydroxy group. In particular, a halogen atom, a nitro group, a cyano group, and an optionally substituted hydrocarbon group are preferred. Examples of the optionally substituted hydrocarbon group include an optionally substituted $C_{1-6}$ alkyl group (preferably, a lower alkyl group substituted by N,N-di-lower alkyl-imino group), and an optionally substituted $C_{6-14}$ aryl group (preferably, a $C_{6-10}$ aryl group). In particular, an optionally substituted methyl and an optionally substituted phenyl are preferred. Among them, an optionally substituted methyl is preferred. Examples of the substituent of "an optionally substituted methyl" are preferably a dimethylimino group. Preferred examples of $R^1$ and $R^{1'}$ include a dimethyliminomethyl group, i.e., a methyl group having a dimethylimino group as a substituent.

In the vinamidinium salt represented by the above formula (I) of the present invention, n represents a number of 2 or more. The number of 2 or more represented by n is preferably 2 to 5. Among them, n is preferably 2 to 3.

In the vinamidinium salt represented by the above formula (I') of the present invention, n represents a number of 1 or more. The number of 1 or more represented by n is preferably 1 to 5. Among them, n is preferably 1 to 3.

$R^2$ and $R^3$ or $R^{2'}$ and $R^{3'}$ are the same or different and each represents a lower alkyl group, or $R^2$ and $R^3$ or $R^{2'}$ and $R^{3'}$ may combine together to form a ring.

Examples of the "lower alkyl group" represented by $R^2$ and $R^3$ or $R^{2'}$ and $R^{3'}$ include a straight or branched $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, 2,2-dimethylbutyl, 3,3-dimethylbutyl, 2-ethylbutyl, heptyl, and octyl. Among them, a $C_{1-6}$ alkyl group is preferred.

$R^2$ and $R^3$ or $R^{2'}$ and $R^{3'}$ may combine together to form a ring and examples of the ring include an aromatic heterocyclic group and a non-aromatic heterocyclic group.

Examples of the non-aromatic heterocyclic group include a 5- or 6-membered monocyclic non-aromatic heterocyclic group and a fused non-aromatic heterocyclic group containing 1 to 4 nitrogen atoms as ring-constituting atoms or a 5- to 6-membered monocyclic non-aromatic heterocyclic group and a fused non-aromatic heterocyclic group containing 1 to 4 heteroatoms selected from an oxygen atom and a sulfur atom in addition to carbon and nitrogen atoms. Examples of the fused aromatic heterocyclic group include those wherein the above 5- to 6-membered monocyclic non-aromatic heterocyclic group is fused to one or two rings such as a 5- or 6-membered ring containing 1 to 2 nitrogen atoms, a 5-membered ring containing one sulfur atom and a benzene ring.

Examples of the non-aromatic heterocyclic group include a monocyclic non-aromatic heterocyclic group such as pyrrolidinyl, piperidinyl, morpholinyl, thiomorpholinyl, piperazinyl, oxazolidinyl, thiazolidinyl, imidazolidinyl, dioxolyl, dioxoranyl, dihydrooxadiazolyl, and tetrahydropyranyl; and a fused non-aromatic heterocyclic group such as dihydroisoindolinyl, 4,5,6,7-tetrahydro-1-benzofuranyl, 4,5,6,7-tetrahydro-1-benzothienyl, indanyl, chromenyl, dihydroisoquinolinyl, tetrahydroisoquinolinyl, dihydrophthalazinyl, pyrazolidinyl, and tetrahydroquinolinyl.

The non-aromatic heterocyclic group is preferably a 5- to 6-membered monocyclic non-aromatic heterocyclic group. Among them, piperidine is preferred.

Preferred examples of $R^2$ and $R^3$ or $R^{2'}$ and $R^{3'}$ include a $C_1$-$C_6$ alkyl. Among them, for example, a methyl group is preferred.

$R^4$ and $R^5$ or $R^{4'}$ and $R^{5'}$ are the same or different and each represents a lower alkyl group, or $R^4$ and $R^5$ or $R^{4'}$ and $R^{5'}$ may combine together to form a ring.

Examples of the "lower alkyl group" represented by $R^4$ and $R^5$ or $R^{4'}$ and $R^{5'}$ include a straight or branched $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, 2,2-dimethylbutyl, 3,3-dimethylbutyl, 2-ethylbutyl, heptyl, and octyl. Among them, a $C_{1-6}$ alkyl group is preferred.

$R^4$ and $R^5$ or $R^{4'}$ and $R^{5'}$ may combine together to form a ring and examples of the ring include an aromatic heterocyclic group or a non-aromatic heterocyclic group.

Examples of the non-aromatic heterocyclic group include a 5- to 7-membered monocyclic non-aromatic heterocyclic group and a fused non-aromatic heterocyclic group having 1 to 5 nitrogen atoms as a ring-constituting atom, or a 5- or 7-membered monocyclic non-aromatic heterocyclic group and a fused non-aromatic heterocyclic group having 1 to 4 heteroatoms selected from an oxygen atom or a sulfur atom in addition to carbon and nitrogen atoms. Examples of the fused non-aromatic heterocyclic group include those wherein the above 5- to 7-membered monocyclic non-aromatic heterocyclic group is fused to one or two rings such as a 5- or 6-membered ring containing 1 to 2 nitrogen atoms, a 5-membered ring containing one sulfur atom and a benzene ring.

Suitable examples of the non-aromatic heterocyclic group include a monocyclic non-aromatic heterocyclic group such as pyrrolidinyl, piperidinyl, morpholinyl, thiomorpholinyl, piperazinyl, hexamethyleneiminyl, oxazolidinyl, thiazolidinyl, imidazolidinyl, dioxolyl, dioxoranyl, dihydrooxadiazolyl, 2-thioxo-1,3-oxazolidin-5-yl, and tetrahydropyranyl; and a fused non-aromatic heterocyclic group such as dihydroisoindolyl, 4,5,6,7-tetrahydro-1-benzofuranyl, 4,5,6,7-tetrahydro-1-benzothienyl, indanyl, chromenyl, dihydroisoquinolinyl, tetrahydroisoquinolinyl, dihydrophthalazinyl, pyrazolidinyl, and tetrahydroquinolinyl.

The non-aromatic heterocyclic group is preferably a 5- to 7-membered monocyclic non-aromatic heterocyclic group. Among them, piperidine is preferred.

Preferred examples of $R^4$ and $R^5$ or $R^{4'}$ and $R^{5'}$ include a $C_1$-$C_6$ alkyl. Among them, for example, a methyl group is preferred.

Specific examples of the vinamidinium salt represented by the formula (I) include 3-(dimethylimino)-2-[(dimethylimino)methyl]-N,N-dimethyl-1-propen-1-aminium trichloride.

$R^6$, $R^7$, $R^8$ and $R^9$ are the same or different and each represents a hydrogen atom or a substituent, or $R^6$ and $R^7$, $R^7$ and $R^8$, or $R^8$ and $R^9$ may combine together to form a 5- to 8-membered ring.

$R^{10}$ represents a hydrogen atom or a substituent;
ring A represents a hydrocarbon ring or a heterocyclic ring; and
ring B represents a benzene ring having substituent(s).

Examples of $R^6$, $R^7$, $R^8$, $R^9$, $R^{10}$, and the "substituent" in ring B include the substituent selected from the group consisting of:
(1) a halogen,
(2) a hydroxy group,
(3) an amino group,
(4) a nitro group,
(5) a cyano group,
(6) an optionally substituted $C_1$-$C_6$ alkyl group,
(7) an optionally substituted $C_2$-$C_6$ alkenyl group,
(8) an optionally substituted $C_2$-$C_6$ alkynyl group,
(9) an optionally substituted $C_3$-$C_6$ cycloalkyl group,
(10) an optionally substituted $C_6$-$C_{14}$ aryl group,
(11) an optionally substituted $C_7$-$C_{16}$ aralkyl group,
(12) an optionally substituted $C_1$-$C_6$ alkoxy group,
(13) an optionally halogenated $C_1$-$C_6$ alkyl group,
(14) an optionally halogenated $C_1$-$C_6$ alkoxy group,
(15) an optionally substituted heterocyclic group,
(16) a $C_2$-$C_6$ alkenyloxy group,
(17) a $C_2$-$C_6$ alkynyloxy group,
(18) a $C_3$-$C_{10}$ cycloalkyloxy group,
(19) a $C_6$-$C_{14}$ aryloxy group,
(20) a $C_7$-$C_{16}$ aralkyloxy group,
(21) a heterocyclic-oxy group,
(22) a heterocyclic-$C_1$-$C_6$ alkyloxy group,
(23) a $C_1$-$C_6$ alkylamino group,
(24) a di($C_1$-$C_6$)alkylamino group,
(25) a $C_6$-$C_{14}$ arylamino group,
(26) a di($C_6$-$C_{14}$)arylamino group,
(27) a $C_7$-$C_{16}$ aralkylamino group,
(28) a di($C_7$-$C_{16}$)aralkylamino group,
(29) a N—($C_1$-$C_6$)alkyl-N—($C_6$-$C_{14}$)arylamino group,
(30) a N—($C_1$-$C_6$)alkyl-N—($C_7$-$C_{16}$)aralkylamino group,
(31) a $C_1$-$C_6$ alkyl-carbonylamino group,
(32) a $C_1$-$C_6$ alkylthio group,
(33) a $C_1$-$C_6$ alkylsulfinyl group,
(34) a $C_1$-$C_6$ alkylsulfonyl group,
(35) an optionally esterified carboxy group,
(36) a $C_1$-$C_6$ alkyl-carbonyl group,
(37) a $C_3$-$C_{10}$ cycloalkyl-carbonyl group,
(38) an optionally substituted $C_6$-$C_{14}$ aryl-carbonyl group,
(39) a $C_7$-$C_{16}$ aralkyl-carbonyl group,
(40) a $C_1$-$C_6$ alkoxy-carbonyl group,
(41) a $C_6$-$C_{14}$ aryloxy-carbonyl group,
(42) a $C_7$-$C_{16}$ aralkyloxy-carbonyl group,
(43) a heterocyclic-carbonyl group,
(44) a thiocarbamoyl group,
(45) a $C_1$-$C_6$ alkyl-carbamoyl group,
(46) a di($C_1$-$C_6$)alkyl-carbamoyl group,
(47) a $C_6$-$C_{14}$ aryl-carbamoyl group,
(48) a di($C_6$-$C_{14}$)aryl-carbamoyl group,
(49) a $C_1$-$C_6$ alkylsulfamoyl group,
(50) a di($C_1$-$C_6$)alkylsulfamoyl group,
(51) a $C_6$-$C_{14}$ arylsulfamoyl group,
(52) a di($C_6$-$C_{14}$)arylsulfamoyl group,
(53) a $C_1$-$C_6$ alkoxyimino group,
(54) a hydroxy-$C_1$-$C_6$ alkyl group, and
(55) a $C_1$-$C_6$ alkoxy-$C_1$-$C_6$ alkyl group.

Examples of the "hydrocarbon ring" represented by ring A include an optionally substituted cycloalkyl group wherein the carbon atom to which the amino group in the formula (II) is attached has a double bond, and an optionally substituted $C_6$-$C_{14}$ aryl group. Examples of the "heterocyclic ring" represented by ring A include an optionally substituted heterocyclic group. Preferred examples of ring A include a phenyl group.

Also, examples of the substituent in ring B include 1 to 5, preferably, 1 to 3 substituents selected from the group consisting of the above (1) to (55).

Examples of the 5- to 8-membered ring formed by $R^6$ and $R^7$, $R^7$ and $R^8$, or $R^8$ and $R^9$ together with the adjacent atom include a $C_3$-$C_6$ cycloalkyl group, a $C_6$-$C_{14}$ aryl group, and a heterocyclic group. Examples of the preferred group of $R^6$, $R^7$, $R^8$ and $R^9$ include a hydrogen atom, or an optionally substituted $C_{1-6}$ alkyl-carbonylamino group (e.g. acetylamino), an optionally substituted $C_{6-14}$ aryl-carbonylamino group (e.g. benzoylamino, and naphthoylamino). Among them, an optionally substituted $C_{6-14}$ aryl-carbonylamino group (e.g. benzoylamino, and naphthoylamino) is preferred. Examples of the preferred group of $R^{10}$ include a methyl group.

The definition of each symbol used herein will be described in detail below.

As used herein, examples of the "halogen" include fluorine, chlorine, bromine, and iodine.

As used herein, examples of the "$C_1$-$C_6$ alkyl group" include methyl, ethyl, propyl, isopropyl, butyl, isobutyl, sec-butyl, tert-butyl, pentyl, isopentyl, neopentyl, tert-pentyl, hexyl, and —$CH_2CH_2C(CH_3)_3$.

As used herein, examples of the "$C_1$-$C_6$ alkenyl group" include vinyl, allyl, propenyl, isopropenyl, but-3-en-1-yl, pent-4-en-1-yl, hex-5-en-1-yl, and 2-methylprop-1-en-yl.

As used herein, examples of the "$C_2$-$C_6$ alkynyl group" include ethynyl, prop-2-yn-1-yl, pent-4-yn-1-yl, and hex-5-yn-1-yl.

As used herein, examples of the "$C_3$-$C_6$ cycloalkyl group" include cyclopropyl, cyclobutyl, cyclopentyl, and cyclohexyl.

As used herein, examples of the "$C_6$-$C_{14}$ aryl group" include phenyl, naphthyl (e.g. 1-naphthyl, 2-naphthyl), anthryl, and phenanthryl, preferably phenyl or naphthyl, and more preferably phenyl.

As used herein, examples of the "$C_7$-$C_{16}$ aralkyl group" include benzyl, 1-phenylethyl, 2-phenylethyl, naphthylmethyl (1-naphthylmethyl, 2-naphthylmethyl), 3-phenylpropyl, 4-phenylbutyl, and 5-phenylpentyl.

As used herein, examples of the "$C_1$-$C_6$ alkoxy group" include methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, and —OCH($CH_2CH_3$)$_2$.

As used herein, examples of the "optionally halogenated $C_1$-$C_6$ alkyl group" include the above "$C_1$-$C_6$ alkyl group" which may be substituted by 1 to 5 "halogens" as described above. Examples thereof include methyl, ethyl, propyl, isopropyl, butyl, tert-butyl, isobutyl, and trifluoromethyl.

As used herein, examples of the "optionally halogenated $C_1$-$C_6$ alkoxy group" include the above "$C_1$-$C_6$ alkoxy group" which may be substituted by 1 to 5 "halogens" as described above. Examples thereof include methoxy, ethoxy, propoxy, isopropoxy, butoxy, tert-butoxy, trifluoromethoxy, and 2-fluoroethoxy.

As used herein, examples of the "heterocyclic group" include a 4- to 14-membered (preferably, 5- to 10-membered) (monocyclic, bicyclic or tricyclic) heterocyclic group containing one to four of 1 or 2 kinds of heteroatoms selected from the group consisting of a nitrogen atom, a sulfur atom and an oxygen atom in addition to carbon atom(s) as a ring-constituting atom, preferably (i) a 5- to 14-membered (preferably, 5- to 10-membered) aromatic heterocyclic group, and (ii) a 4- to 10-membered (preferably, 5- to 10-membered) non-aromatic heterocyclic group, unless otherwise noted.

Examples of the "aromatic heterocyclic group" include a monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyradinyl, and triadinyl; and an aromatic fused heterocyclic group such as benzofuryl, isobenzofuryl, benzo[b]thienyl, indolyl, isoindolyl, 1H-indazolyl, benzimidazolyl, benzoxazolyl, benzo[d]isoxazolyl, benzothiazolyl, benzo[d]isothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxatiynyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazinyl, imidazo[1,2-a]pyrimidinyl, 1,2,4-triazo[4,3-a]pyridyl, and 1,2,4-triazo[4,3-b]pyridazinyl.

Examples of the "non-aromatic heterocyclic group" include a monocyclic non-aromatic heterocyclic group such as azetidinyl, oxetanyl, thietanyl, pyrrolidinyl, tetrahydrofuryl, thioranyl, imidazolidinyl, pyrazolidinyl, oxazolidinyl, thiazolidinyl, piperidyl, tetrahydropyranyl, morpholinyl, thiomorpholinyl, and piperadinyl; a non-aromatic fused heterocyclic group such as isochromanyl, dihydrobenzopyranyl, isochromenyl, chromenyl (2H-chromenyl, 4H-chromenyl), 1,2,3,4-tetrahydroisoquinolyl, 1,2,3,4-tetrahydroquinolyl, 2,3-dihydrobenzofuranyl, and 1,3-benzodioxolyl.

As used herein, examples of the "$C_2$-$C_6$ alkenyloxy group" include vinyloxy, allyloxy, propenyloxy, isopropenyloxy, but-3-en-1-yloxy, pent-4-en-1-yloxy, and hex-5-en-1-yloxy.

As used herein, examples of the "$C_2$-$C_6$ alkynyloxy group" include ethynyloxy, prop-2-yn-1-yloxy, but-3-yn-1-yloxy, pent-4-yn-1-yloxy, hex-5-yn-1-yloxy, and 1-methylbut-3-yn-1-yloxy.

As used herein, examples of the "$C_3$-$C_{10}$ cycloalkyloxy group" include cyclopropyloxy, cyclobutyloxy, cyclopentyloxy, cyclohexyloxy, cycloheptyloxy, and cyclooctyloxy.

As used herein, examples of the "$C_6$-$C_{14}$ aryloxy group" include phenoxy, 1-naphthyloxy, and 2-naphthyloxy.

As used herein, examples of the "$C_7$-$C_{16}$ aralkyloxy group" include benzyloxy, and phenetyloxy.

As used herein, examples of the "heterocyclic-oxy group" include a heterocyclic-oxy group wherein the heterocyclic moiety is a 5- or 6-membered aromatic or non-aromatic heterocyclic ring containing one to four of 1 to 2 kinds of heteroatoms selected from the group consisting of a nitrogen atom, a sulfur atom and an oxygen atom in addition to carbon atom(s) as a ring-constituting atom. Suitable examples of the "heterocyclic-oxy group" include tetrahydrofuranyloxy (e.g. tetrahydrofuran-3-yloxy), tetrahydropyranyloxy (e.g. tetrahydropyran-4-yloxy), and piperidinyloxy (e.g. piperidin-4-yloxy).

As used herein, examples of the "heterocyclic-$C_1$-$C_6$ alkyloxy group" include a heterocyclic-($C_1$-$C_6$) alkyloxy group wherein the heterocyclic moiety is a 5- or 6-membered aromatic or non-aromatic heterocyclic ring containing one to four of 1 or 2 kinds of heteroatoms selected from the group consisting of a nitrogen atom, a sulfur atom and an oxygen atom in addition to carbon atom(s) as a ring-constituting atom. Suitable examples of the "heterocyclic-$C_1$-$C_6$ alkyloxy group" include tetrahydrofuranylmethoxy (e.g. tetrahydrofuran-3-ylmethoxy), tetrahydropyranylmethoxy (e.g. tetrahydropyran-4-ylmethoxy), and piperidinylmethoxy (e.g. piperidin-4-ylmethoxy).

As used herein, examples of the "$C_1$-$C_6$ alkylamino group" include an amino group mono-substituted by the above "$C_1$-$C_6$ alkyl group". Examples thereof include methylamino, ethylamino, propylamino, isopropylamino, butylamino, isobutylamino, sec-butylamino, tert-butylamino, pentylamino, isopentylamino, neopentylamino, tert-pentylamino, and hexylamino.

As used herein, examples of the "di($C_1$-$C_6$) alkylamino group" include an amino group di-substituted by the above "$C_1$-$C_6$ alkyl group". Examples thereof include dimethylamino, diethylamino, and N-ethyl-N-methylamino.

As used herein, examples of the "$C_6$-$C_{14}$ arylamino group" include an amino group mono-substituted by the above "$C_6$-$C_{14}$ aryl group". Examples thereof include phenylamino, 1-naphthylamino, and 2-naphthylamino.

As used herein, examples of the "di($C_6$-$C_{14}$) arylamino group" include an amino group di-substituted by the above "$C_6$-$C_{14}$ aryl group". Examples thereof include diphenylamino, and dinaphthylamino.

As used herein, examples of the "$C_7$-$C_{16}$ aralkylamino group" include an amino group mono-substituted by the above "$C_7$-$C_{16}$ aralkyl group". Examples thereof include benzylamino, and phenethylamino.

As used herein, examples of the "di($C_7$-$C_{16}$) aralkylamino group" include an amino group di-substituted by the above "$C_7$-$C_{16}$ aralkyl group". Examples thereof include dibenzylamino, and diphenethylamino.

As used herein, examples of the "N—($C_1$-$C_6$) alkyl-N—($C_6$-$C_{14}$) arylamino group" include an amino group substituted by the above "$C_1$-$C_6$ alkyl group" and the above "$C_6$-$C_{14}$ aryl group". Examples thereof include N-methyl-N-phenylamino, and N-ethyl-N-phenylamino.

As used herein, examples of the "N—($C_1$-$C_6$) alkyl-N—($C_7$-$C_{16}$ aralkylamino group" include an amino group substituted by the above "$C_1$-$C_6$ alkyl group" and the above "$C_7$-$C_{16}$ aralkyl group". Examples thereof include N-methyl-N-benzylamino, and N-ethyl-N-benzylamino.

As used herein, examples of the "$C_1$-$C_6$ alkyl-carbonylamino group" include acetylamino, propanoylamino, butanoylamino, 2-methylpropanoylamino, pentanoylamino, 3-methylbutanoylamino, and 2,2-dimethylpropanoylamino.

As used herein, examples of the "$C_1$-$C_6$ alkylthio group" include methylthio, ethylthio, propylthio, isopropylthio, butylthio, sec-butylthio, and tert-butylthio.

As used herein, examples of the "$C_1$-$C_6$ alkylsulfinyl group" include methylsulfinyl, ethylsulfinyl, propylsulfinyl, isopropylsulfinyl, butylsulfinyl, sec-butylsulfinyl, and tert-butylsulfinyl.

As used herein, examples of the "$C_1$-$C_6$ alkylsulfonyl group" include methylsulfonyl, ethylsulfonyl, propylsulfonyl, isopropylsulfonyl, butylsulfonyl, sec-butylsulfonyl, and tert-butylsulfonyl.

As used herein, examples of the "optionally esterified carboxy group" include a carboxy group, a $C_1$-$C_6$ alkoxy-carbonyl group (e.g. methoxycarbonyl, ethoxycarbonyl, propoxycarbonyl, and tert-butoxycarbonyl), a $C_6$-$C_{14}$ aryloxy-carbonyl group (e.g. phenoxycarbonyl), a $C_7$-$C_{16}$ aralkyloxycarbonyl group (e.g. benzyloxycarbonyl, and phenethyloxycarbonyl).

As used herein, examples of the "$C_1$-$C_6$ alkyl-carbonyl group" include acetyl, propanoyl, butanoyl, 2-methylpropanoyl, pentanoyl, 3-methylbutanoyl, and 2,2-dimethylpropanoyl.

As used herein, examples of the "$C_3$-$C_{10}$ cycloalkyl-carbonyl group" include cyclopentylcarbonyl, cyclohexylcarbonyl, and adamantylcarbonyl.

As used herein, examples of the "$C_6$-$C_{14}$ aryl-carbonyl group" include benzoyl, 1-naphthoyl, and 2-naphthoyl.

As used herein, examples of the "$C_7$-$C_{16}$ aralkyl-carbonyl group" include phenylacetyl, and 3-phenylpropanoyl.

As used herein, examples of the "a$C_1$-$C_6$ lkoxy-carbonyl group" include methoxycarbonyl, ethoxycarbonyl, propoxycarbonyl, and tert-butoxycarbonyl.

As used herein, examples of the "$C_6$-$C_{14}$ aryloxy-carbonyl group" include phenoxycarbonyl, 1-naphthyloxycarbonyl, and 2-naphthyloxycarbonyl.

As used herein, examples of the "$C_7$-$C_{16}$ aralkyloxy-carbonyl group" include benzyloxycarbonyl, and phenethyloxycarbonyl.

As used herein, examples of the "heterocyclic-carbonyl group" include those wherein the heterocyclic moiety is a 5- or 6-membered aromatic or non-aromatic heterocyclic ring containing one to four of 1 or 2 kinds of heteroatoms selected from the group consisting of a nitrogen atom, a sulfur atom and an oxygen atom in addition to carbon atom(s) as a ring-constituting atom. Suitable examples of the "heterocyclic-carbonyl group" include 1-pyrrolidinylcarbonyl, piperidinocarbonyl, 1-piperadinylcarbonyl, morpholinocarbonyl, and thiomorpholinocarbonyl.

As used herein, examples of the "thiocarbamoyl group" include a thiocarbamoyl group mono-substituted by the above "$C_1$-$C_6$ alkyl group". Examples thereof include methylthiocarbamoyl, and ethylthiocarbamoyl.

As used herein, examples of the "$C_1$-$C_6$ alkyl-carbamoyl group" include a carbamoyl group mono-substituted by the above "$C_1$-$C_6$ alkyl group". Examples thereof include methylcarbamoyl, and ethylcarbamoyl.

As used herein, examples of the "di($C_1$-$C_6$) alkyl-carbamoyl group" include a carbamoyl group di-substituted by the above "$C_1$-$C_6$ alkyl group". Examples thereof include dimethylcarbamoyl, diethylcarbamoyl, and N-ethyl-N-methylcarbamoyl.

As used herein, examples of the "$C_6$-$C_{14}$ aryl-carbamoyl group" include a carbamoyl group mono-substituted by the above "$C_6$-$C_{14}$ aryl group". Examples thereof include phenylcarbamoyl, 1-naphthylcarbamoyl, and 2-naphthylcarbamoyl.

As used herein, examples of the "di($C_6$-$C_{14}$) aryl-carbamoyl group" include a carbamoyl group di-substituted by the above "$C_6$-$C_{14}$ aryl group". Examples thereof include diphenylcarbamoyl, and dinaphthylcarbamoyl.

As used herein, examples of the "$C_1$-$C_6$ alkylsulfamoyl group" include a sulfamoyl group mono-substituted by the above "$C_1$-$C_6$ alkyl group". Examples thereof include methylsulfamoyl, and ethylsulfamoyl.

As used herein, examples of the "di($C_1$-$C_6$) alkylsulfamoyl group" include a sulfamoyl group di-substituted by the above "$C_1$-$C_6$ alkyl group". Examples thereof include dimethylsulfamoyl, diethylsulfamoyl, and N-ethyl-N-methylsulfamoyl.

As used herein, examples of the "$C_6$-$C_{14}$ arylsulfamoyl group" include a sulfamoyl group mono-substituted by the above "$C_6$-$C_{14}$ aryl group". Examples thereof include phenylsulfamoyl, 1-napthylsulfamoyl, and 2-napthylsulfamoyl.

As used herein, examples of the "di($C_6$-$C_{14}$) arylsulfamoyl group" include a sulfamoyl group di-substituted by the above "$C_6$-$C_{14}$ aryl group". Examples thereof include diphenylsulfamoyl, and dinaphthylsulfamoyl.

As used herein, examples of the "$C_1$-$C_6$ alkoxyimino group" include methoxyimino, ethoxyimino, propoxyimino, isopropoxyimino, butoxyimino, isobutoxyimino, sec-butoxyimino, tert-butoxyimino, pentyloxyimino, and hexyloxyimino.

As used herein, examples of the "hydroxy-$C_1$-$C_6$ alkyl group" include hydroxymethyl, 2-hydroxyethyl, 1-hydroxyethyl, 3-hydroxypropyl, and 1-hydroxy-1-methylethyl.

As used herein, examples of the "$C_1$-$C_6$ alkoxy-$C_1$-$C_6$ alkyl group" include methoxymethyl, 2-methoxyethyl, 1-methoxyethyl, ethoxymethyl, and 2-ethoxyethyl.

Crystals of the trivalent vinamidinium salt having halogen anions of the present invention are free from hygroscopicity and deliquescent nature, and hence they are stable and are excellent in storage stability. Therefore, the salt is characterized in that it can be produced industrially.

In addition, specific examples of the vinamidinium salt represented by the formula (I') include 2-dimethylaminomethylene-1,3-bis(dimethyliminio)propane dichloride. An acetic acid solution of the vinamidinium salt represented by the formula (I') is also characterized in that it is excellent in storage stability.

Further, as seen from the results of Comparative Example 1 hereinafter, the vinamidinium salt having halogen anions of the present invention has very high reaction selectivity in the construction reaction of quinoline skeleton and the like as compared with the reaction using a salt such as $PF_6$ salt, $BF_4$ salt or $ClO_4$ salt.

The vinamidinium salt represented by the formula (I) can be produced, for example, by the following process.

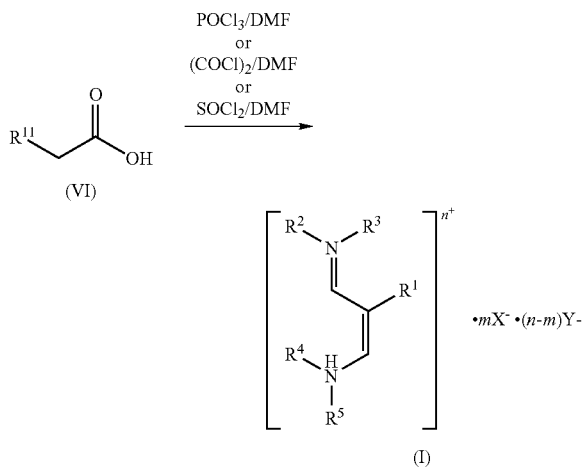

wherein $R^{11}$ represents a chlorine atom or a bromine atom, when $R^1$ is a dimethyliminomethyl group, otherwise it is the same as $R^1$, DMF represents N,N-dimethylformamide, and the other symbols are as defined above.

If the compound represented by the formula (VI) is commercially available, a commercially available product can be used as it is. Alternatively, the compound represented by the formula (VI) can be produced by a per se known method or a modification thereof.

Usually, phosphorus oxychloride ($POCl_3$), oxalyl chloride ($(COCl)_2$) or thionyl chloride ($SOCl_2$) can be used in an amount of about 0.1 to 100 mol, preferably, about 1 to 10 mol per mol of the compound represented by the formula (VI).

N,N-dimethylformamide (DMF) is usually used in an amount of about 0.1 to 100 mol, preferably about 1 to 10 mol per mole of the compound represented by the formula (VI).

The reaction temperature is usually about −70 to 200° C., preferably, about 0 to 150° C.

The reaction time is usually about 0.5 hour to 1 week, preferably, about 0.5 to 24 hours.

The compound represented by the formula (I) thus obtained can be isolated from a reaction mixture and purified by a per se known separation means (e.g. concentration, concentration under reduced pressure, solvent extraction, crystallization, recrystallization, re-extraction, and chromatography). In particular, crystallization is preferably used for isolation of the compound represented by the formula (I).

Examples of the solvent used for crystallization include aliphatic hydrocarbons (e.g. hexane, pentane, cyclohexane, and heptane), aromatic hydrocarbons (e.g. benzene, toluene, xylene, and chlorobenzene), ethers (e.g. diethyl ether, diisopropyl ether, tert-butyl methyl ether, diphenyl ether, tetrahydrofuran, dioxane, and 1,2-dimethoxyethane), halogenated hydrocarbons (e.g. dichloromethane, chloroform, 1,2-dichloroethane, and carbon tetrachloride), esters (e.g. ethyl acetate, and n-butyl acetate), ketones (e.g. acetone, and methyl ethyl ketone), nitriles (e.g. acetonitrile, and propionitrile), sulfoxides (e.g. dimethyl sulfoxide), amides (e.g. N,N-dimethylformamide, N,N-dimethylacetoamide, N-methylpyrrolidone, and hexamethylphosphoric triamide), carboxylic acids (e.g. acetic acid, and propionic acid), alcohols (e.g. methanol, ethanol, isopropyl alcohol, 1-butanol, isobutanol, tert-butanol, and 2-methyl-2-butanol), and water. They can be used alone or as a mixture of two or more thereof.

The compound represented by the formula (I) can be obtained by carrying out an "acid treatment" during the reaction or at an isolation stage of the product. The "acid treatment" is preferably carried out at the isolation stage of the compound. Specifically, the "acid treatment" is carried out by addition of, for example, an enough amount of hydrogen chloride or hydrogen bromide. Hydrogen chloride or hydrogen bromide used may be in a gaseous state or a solution state.

The enough amount used herein means an amount enough for protonation or cationization of all groups present in the compound represented by the formula (I) which can be protonated or cationized.

The crystallization is preferably carried out under the following conditions.

The crystallization temperature is usually about −70 to 100° C., preferably, about 0 to 40° C.

The crystallization time is usually about 0.5 to 48 hours, preferably, about 0.5 to 24 hours.

Crystals obtained by the crystallization can be isolated by carrying out filtration and drying. Since an excess amount of the acid adheres to wet crystals obtained by filtration, aeration-drying with nitrogen or argon gas of low humidity is carried out to volatilize the acid. The dew point of nitrogen or argon gas for using aeration-drying is preferably −40° C. or lower, more preferably, −60° C. or lower.

Hereinafter, synthetic methods of quinoline derivatives using the vinamidinium salt of the present invention will be explained.

1. Synthetic Method of Substituted Quinoline Derivative (a) A Method Using the Vinamidinium Salt Represented by the Formula (I)

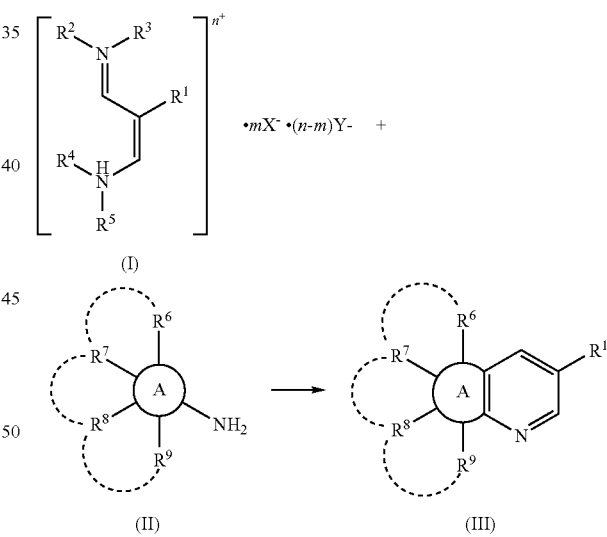

The above vinamidinium salt represented by the formula (I) can be reacted with a compound represented by the formula (II) to synthesize a quinoline derivative represented by the formula (III).

In the formula (II) and the formula (III), the ring A represents a hydrocarbon ring or a heterocyclic ring wherein the carbon atom to which the amino group in the formula (II) is attached has a double bond. $R^2R^3$, $R^4$ and $R^5$ are the same or different and each represents a hydrogen atom or a substituent, or $R^2$ and $R^3$, $R^3$ and $R^4$, or $R^4$ and $R^5$ may combine together with the adjacent atom to form a 5- to 8-membered ring. Examples of the "substituent" include an optionally substituted hydrocarbon group, an optionally substituted heterocyclic group, and the same group as the substituent of the "optionally substituted hydrocarbon group" represented by the above $R^1$ and $R^{1'}$. Examples of the "optionally substituted hydrocarbon group" include the same group as the above "optionally substituted hydrocarbon group" represented by $R^1$ and $R^{1'}$. Examples of the "optionally substituted heterocyclic group" include the same group as the above "optionally substituted heterocyclic group" represented by $R^1$ and $R^{1'}$.

Preferably, $R^2$, $R^3$, $R^4$ and $R^5$ are a hydrogen atom, an optionally substituted hydrocarbon group, a halogen atom (e.g. fluorine, chlorine, bromine, and iodine), a nitro group, a nitroso group, a cyano group, a $C_{1-6}$ alkoxy group (e.g. methoxy, ethoxy, propoxy, isopropoxy, butoxy, isobutoxy, sec-butoxy, pentyloxy, and hexyloxy), a $C_{1-6}$ alkyl-carbonylamino group (e.g. acetylamino) and a $C_{6-14}$ aryl-carbonylamino group (e.g. benzoylamino, and naphthoylamino). Among them, preferred are a hydrogen atom, a $C_{1-6}$ alkyl group (e.g. methyl, ethyl, propyl, isopropyl, butyl, isobutyl, sec-butyl, tert-butyl, pentyl, and hexyl), a $C_{1-6}$ alkyl-carbonylamino group (e.g. acetylamino), and a $C_{6-14}$ aryl-carbonylamino group (e.g. benzoylamino and naphthoylamino).

Further, examples of the 5- to 8-membered ring formed by $R^2$ and $R^3$, $R^3$ and $R^4$, or $R^4$ and $R^5$ together with adjacent atom include cyclopentene, cyclohexene, cycloheptene, cyclooctene, cyclopentadiene, benzene, pyrrole, pyridine, furan, thiophene, imidazole, pyrazole, oxazole, isoxazole, thiazole, isothiazole, pyridazine, pyrimidine and pyrazine.

Preferred examples of the compound represented by the formula (II) include those wherein $R^2$ and $R^3$ are a hydrogen atom, $R^4$ is a $C_{1-6}$ alkyl-carbonylamino group (e.g. acetylamino), or aryl-carbonylamino group (e.g. a $C_{6-14}$ benzoylamino, or naphthoylamino), and $R^5$ is a hydrogen atom or a $C_{1-6}$ alkyl group (e.g. methyl, ethyl, propyl, isopropyl, butyl, isobutyl, sec-butyl, tert-butyl, pentyl or hexyl). Specifically, for example, N-(3-aminophenyl)acetamide is preferred.

In addition, in the formula (III), $R^1$ is as defined with respect to the formula (I).

If the compound represented by the formula (II) is commercially available, a commercially available product can be used as it is. Alternatively, the compound represented by the formula (II) can be produced by a per se known method or a modification thereof.

The compound represented by the formula (I) can be used in an amount of about 0.1 to 10 mol, preferably, about 1 to 5 mol per mol of the compound represented by the formula (II).

This reaction is optionally and preferably carried out with addition of a base. Examples of the "base" include triethylamine, diisopropylethylamine, diethylamine, dipropylamine, diisopropylamine, dibutylamine, diisobutylamine, butylamine, pyridine, pyrrolidine, piperidine, morpholine, sodium carbonate, potassium carbonate, sodium hydroxide, potassium hydroxide, sodium methoxide, potassium methoxide, sodium tert-butoxide, and potassium tert-butoxide.

This reaction is optionally and preferably carried out in an inert solvent for the reaction.

Examples of the "inert solvent for the reaction" include aliphatic hydrocarbons (e.g. hexane, pentane, cyclohexane and heptane), aromatic hydrocarbons (e.g. benzene, toluene, xylene, and chlorobenzene), ethers (e.g. diethyl ether, diisopropyl ether, tert-butyl methyl ether, diphenyl ether, tetrahydrofuran, dioxane, and 1,2-dimethoxyethane), halogenated hydrocarbons (e.g. dichloromethane, chloroform, 1,2-dichloroethane, and carbon tetrachloride), esters (e.g. ethyl acetate, and n-butyl acetate), ketones (e.g. acetone, and methyl ethyl ketone), nitriles (e.g. acetonitrile, and propionitrile), sulfoxides (e.g. dimethylsulfoxide), amides (e.g. N,N-dimethylformamide, N,N-dimethylacetamide, N-methylpyrrolidone, and hexamethylphosphoric triamide), carboxylic acids (e.g. acetic acid, and propionic acid), alcohols (e.g. methanol, ethanol, isopropyl alcohol, 1-butanol, isobutanol, tert-butanol, and 2-methyl-2-butanol) and water. They can be used alone or as a mixture of two or more thereof.

The reaction temperature is usually about −70 to 200° C., preferably about 50 to 150° C.

The reaction time is usually 0.5 hours to 2 weeks, preferably about 0.5 to 72 hours.

The compound represented by the formula (III) thus obtained can be isolated from a reaction mixture and purified by a per se known separation means (e.g. concentration, concentration under reduced pressure, solvent extraction, crystallization, recrystallization, re-extraction, and chromatography). In particular, crystallization is preferably used for isolation of the compound represented by the formula (III).

The same solvent as the above "inert solvent" used for the reaction of the compound represented by the formula (I) with the compound represented by the formula (II) can be used as a solvent used for the crystallization, The crystallization temperature is usually about −70 to 100° C., preferably about 0 to 40° C.

The crystallization time is usually about 0.5 to 48 hours, preferably about 0.5 to 24 hours.

(b) A Method Using an Acetic Acid Solution of the Vinamidinium Salt Represented by the Formula (I')

The quinoline derivative represented by the formula (III') can be synthesized by reacting an acetic acid solution of the vinamidinium salt represented by the above formula (I') with the compound represented by the above formula (II). In the formula (III'), $R^{1'}$ is as defined with respect to the formula (I'), and $R^2$, $R^3$, $R^4$ and $R^5$ are as defined with respect to the formula (II).

An acetic acid solution of the vinamidinium salt represented by the formula (I') may be mixed with the acetic acid solution of the vinamidinium salt represented by the formula (I) in an arbitrary ratio.

If the compound represented by the formula (II) is commercially available, a commercially available product can be used as it is. Alternatively, the compound represented by the formula (II) can be produced by a per se known method or a modification thereof.

The compound represented by the formula (I') can be used in an amount of about 0.1 to 10 mol, preferably about to 5 mol per mol of the compound represented by the formula (II).

The reaction temperature is usually about −70 to 200° C., preferably about 50 to 150° C.

The reaction time is usually 0.5 hours to 2 weeks, preferably about 0.5 to 72 hours.

The compound represented by the formula (III') thus obtained can be isolated from a reaction mixture and purified by a per se known separation means (e.g. concentration, concentration under reduced pressure, solvent extraction, crystallization, recrystallization, re-extraction, and chromatography). In particular, crystallization is preferably used for isolation of the compound represented by the formula (III').

The above "inert solvent" used for the reaction of the compound represented by the formula (I) with the compound represented by the formula (II) can be used as a solvent used for the crystallization, The crystallization temperature is usually about −70 to 100° C., preferably about 0 to 40° C.

The crystallization time is usually about 0.5 to 48 hours, preferably about 0.5 to 24 hours.

2. Synthetic Method of Tri-Substituted Quinoline Derivative (a) A Method Using the Vinamidinium Salt Represented by the Formula (I)

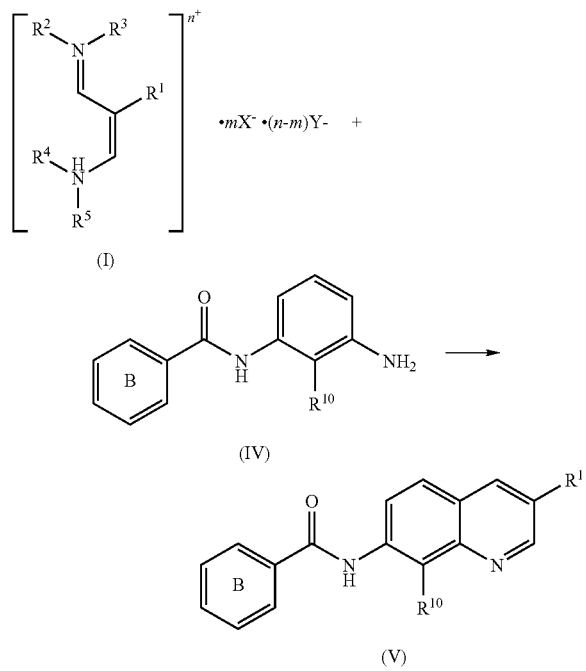

The quinoline derivative represented by the formula (V) can be synthesized by reacting the vinamidinium salt represented by the formula (I) with the compound of the formula (IV).

In the formula (IV) and the formula (V), $R^{10}$ represents a hydrogen atom or a substituent, and the ring B represents a substituted benzene ring.

Examples of the "substituent" represented by $R^{10}$ include an optionally substituted hydrocarbon group, an optionally substituted heterocyclic group, and the same group as the substituent of the "optionally substituted hydrocarbon group" represented by the above $R^1$ and $R^{1'}$. Examples of the "optionally substituted hydrocarbon group" include the same group as the "optionally substituted hydrocarbon group" represented by the above $R^1$ and $R^{1'}$. Examples of the "optionally substituted heterocyclic group" include the same group as the "optionally substituted heterocyclic group" represented by the above $R^1$ and $R^{1'}$.

Preferred examples of $R^{10}$ include a hydrogen atom, an optionally substituted hydrocarbon group, a halogen atom (e.g. fluorine, chlorine, bromine, and iodine), a nitro group, a nitroso group, a cyano group, a $C_{1-6}$ alkoxy group (e.g. methoxy, ethoxy, propoxy, isopropoxy, butoxy, isobutoxy, sec-butoxy, pentyloxy, and hexyloxy), a $C_{1-6}$ alkyl-carbonylamino group (e.g. acetylamino) and a $C_{6-14}$ aryl-carbonylamino group (e.g. benzoylamino, and naphthoylamino). Among them, preferred are a hydrogen atom, a $C_{1-6}$ alkyl group (e.g. methyl, ethyl, propyl, isopropyl, butyl, isobutyl, sec-butyl, tert-butyl, pentyl, and hexyl), a $C_{1-6}$ alkyl-carbonylamino group (e.g. acetylamino), and a $C_{6-14}$ aryl-carbonylamino group (e.g. benzoylamino and naphthoylamino). In particular, a hydrogen atom, and a $C_{1-6}$ alkyl group (e.g. methyl, ethyl, propyl, isopropyl, butyl, isobutyl, sec-butyl, tert-butyl, pentyl, and hexyl) are preferred, with a hydrogen atom and a methyl group being particularly preferred.

Examples of the substituent of the ring B include the same group as the "substituent" represented by the above $R^{10}$. The ring B has 1 to 3 substituents selected from these substituents at possible positions. The number of the substituents is preferably 1, and the substituent at the para position is more preferred. Preferred examples of the substituent include a halogen atom (e.g. fluorine, chlorine, bromine, and iodine), a nitro group, a nitroso group, a cyano group, an optionally substituted hydrocarbon group, a $C_{1-6}$ alkoxy group (e.g. methoxy, ethoxy, propoxy, isopropoxy, butoxy, isobutoxy, sec-butoxy, pentyloxy, and hexyloxy), a $C_{1-6}$ alkyl-carbonylamino group (e.g. acetylamino), and $C_{6-14}$ aryl-carbonylamino group (e.g. benzoylamino, and naphthoylamino). Among them, a $C_{1-6}$ alkoxy group (e.g. methoxy, ethoxy, propoxy, isopropoxy, butoxy, isobutoxy, sec-butoxy, pentyloxy, and hexyloxy) is preferred, with a cyclopropylmethoxy group being particularly preferred.

Examples of the compound represented by the formula (IV) include those wherein $R^{10}$ is a hydrogen atom or a $C_{1-6}$ alkyl group (e.g. methyl, ethyl, propyl, isopropyl, butyl, isobutyl, sec-butyl, tert-butyl, pentyl, and hexyl), and the ring B has a $C_{1-6}$ alkoxy group (e.g. methoxy, ethoxy, propoxy, isopropoxy, butoxy, isobutoxy, sec-butoxy, pentyloxy, and hexyloxy) as a substituent at the para position. Specific examples thereof include N-(3-amino-2-methylphenyl)-4-(cyclopropylmethoxy)benzoic acid amide.

Further, in the formula (V), $R^1$ is as defined with respect to the formula (I).

If the compound represented by the formula (IV) is commercially available, a commercially available product can be used as it is. Alternatively, the compound represented by the formula (IV) can be produced by a per se known method or a modification thereof.

The compound represented by the formula (I) can be used in an amount of about 0.1 to 10 mol, preferably about to 5 mol per mol of the compound represented by the formula (IV).

This reaction is optionally and preferably carried out by addition of a base. Examples of the "base" include triethylamine, diisopropylethylamine, diethylamine, dipropylamine, diisopropylamine, dibutylamine, diisobutylamine, butylamine, pyridine, pyrrolidine, piperidine, morpholine, sodium carbonate, potassium carbonate, sodium hydroxide, potassium hydroxide, sodium methoxide, potassium methoxide, sodium tert-butoxide, and potassium tert-butoxide. Among them, morpholine, piperidine, diethylamine, dipropylamine, diiospropylamine, dibutylamine, and diisobutylamine are preferred.

This reaction is optionally and preferably carried out in an inert solvent for the reaction.

Examples of the "inert solvent for the reaction" include aliphatic hydrocarbons (e.g. hexane, pentane, cyclohexane, and heptane), aromatic hydrocarbons (e.g. benzene, toluene, xylene, and chlorobenzene), ethers (e.g. diethyl ether, diisopropyl ether, tert-butyl methyl ether, diphenyl ether, tetrahydrofuran, dioxane, and 1,2-dimethoxyethane), halogenated hydrocarbons (e.g. dichloromethane, chloroform, 1,2-dichloroethane, and carbon tetrachloride), esters (e.g. ethyl acetate, and n-butyl acetate), ketones (e.g. acetone, and methyl ethyl ketone), nitriles (e.g. acetonitrile, and propionitrile), sulfoxides (e.g. dimethylsulfoxide), amides (e.g. N,N-dimethylformamide, N,N-dimethylacetamide, N-methylpyrrolidone, and hexamethylphosphoric triamide), carboxylic acids (e.g. acetic acid, and propionic acid), alcohols (e.g. methanol, ethanol, isopropyl alcohol, 1-butanol, isobutanol, tert-butanol, and 2-methyl-2-butanol) and water. They can be used alone or as a mixture of two or more thereof. Among them, alcohols are preferred, with methanol, ethanol, isopropyl alcohol, 1-butanol, isobutanol, tert-butanol and 2-methyl-2-butanol being particularly preferred.

The reaction temperature is usually about −70 to 200° C., preferably about 50 to 150° C.

The reaction time is usually 0.5 hours to 2 weeks, preferably about 0.5 to 72 hours.

The compound represented by the formula (V) thus obtained can be isolated from a reaction mixture and purified by a per se known separation means (e.g. concentration, concentration under reduced pressure, solvent extraction, crystallization, recrystallization, re-extraction, and chromatography). In particular, crystallization is preferably used for isolation of the compound represented by the formula (V).

The above "inert solvent" used for the reaction of the compound represented by the formula (I) with the compound represented by the formula (IV) can be used as a solvent used for the crystallization, The crystallization temperature is usually about −70 to 100° C., preferably about 0 to 40° C.

The crystallization time is usually about 0.5 to 48 hours, preferably about 0.5 to 24 hours.

In this reaction, when a compound wherein $R^1$ is a lower alkyl group substituted with N,N-di-lower alkyl-imino group is used as the starting compound, sometimes, it becomes aldehyde or a lower alkyl group substituted with aldehyde in the end product.

(b) A Method Using an Acetic Acid Solution of the Vinamidinium Salt Represented by the Formula (I')

The quinoline derivative represented by the formula (V') can be synthesized by reacting an acetic acid solution of the vinamidinium salt represented by the formula (I') with the compound of the formula (IV). In the formula (V'), $R^{1'}$ is as defined with respect to the formula (I'), and the ring A is as defined with respect to the formula (IV).

An acetic acid solution of the vinamidinium salt represented by the formula (I') may be mixed with the acetic acid solution of the vinamidinium salt represented by the formula (I) in an arbitrary ratio.

If the compound represented by the formula (IV) is commercially available, a commercially available product can be used as it is. Alternatively, the compound represented by the formula (IV) can be produced by a per se known method or a modification thereof.

The compound represented by the formula (I') can be used in an amount of about 0.1 to 10 mol, preferably about to 5 mol per mol of the compound represented by the formula (IV).

The reaction temperature is usually about −70 to 200° C., preferably about 50 to 150° C.

The reaction time is usually 0.5 hours to 2 weeks, preferably about 0.5 to 72 hours.

The compound represented by the formula (V') thus obtained can be isolated from a reaction mixture and purified by a per se known separation means (e.g. concentration, concentration under reduced pressure, solvent extraction, crystallization, recrystallization, re-extraction, and chromatography). In particular, crystallization is preferably used for isolation of the compound represented by the formula (V').

The above "inert solvent" used for the reaction of the compound represented by the formula (I) with the compound represented by the formula (IV) can be used as a solvent used for the crystallization, The crystallization temperature is usually about −70 to 100° C., preferably about 0 to 40° C.

The crystallization time is usually about 0.5 to 48 hours, preferably about 0.5 to 24 hours.

In this reaction, when a compound wherein $R^{1'}$ is a lower alkyl group substituted with N,N-di-lower alkyl-imino group is used as the starting compound, sometimes, it becomes aldehyde or a lower alkyl group substituted with aldehyde in the end product.

Hereinafter, the present invention will be explained in more detail by means of Examples and Comparative Example. However, the present invention is not limited thereto.

EXAMPLE 1

3-(Dimethylimino)-2-[(dimethylimino)methyl]-N,N-dimethyl-1-propene-1-aminium trichloride

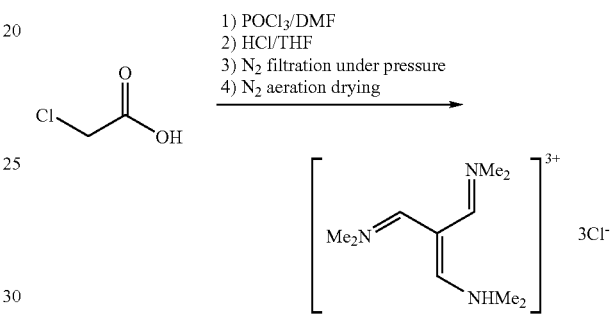

Chloroacetic acid (40 g) was added to N,N-dimethylformamide (186 g) and dissolved therein. Phosphorus oxychloride (260 g) was added dropwise thereto with cooling. Then, the resulting mixture was heated to 85° C., followed by stirring for 1 hour. The temperature was raised to 95° C. and the mixture was stirred for 1 hour. Further, the temperature was raised to 105° C. and the mixture was stirred for 1 hour, followed by cooling to room temperature. Conc. hydrochloric acid (71 mL) and tetrahydrofuran (800 mL) were added dropwise thereto at the same temperature and the resulting mixture was stirred for 1 hour. Precipitated crystals were collected by filtration under pressure in an atmosphere of nitrogen (dew point: about −65° C.) and washed with a mixture of tetrahydrofuran/ethanol (120 mL/20 mL). Subsequently, the crystals were dried by aeration with nitrogen (dew point: about −65° C.) to obtain the title compound (51 g).

Elemental analysis: $C_{10}H_{22}N_3Cl_3 \cdot H_2O$
Calcd: C, 38.91; H, 7.84; N, 13.61; Cl, 34.36.
Found: C, 38.56; H, 8.21; N, 13.63; Cl, 34.58.
m.p. 129-131° C.

EXAMPLE 2

3-(Dimethylimino)-N,N-dimethyl-2-phenyl-1-propene-1-aminium dibromide

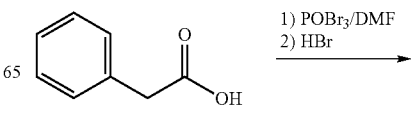

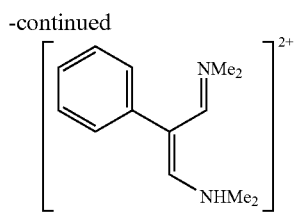

Phenylacetic acid (11.9 g) was added to N,N-dimethylformamide (14 g) and dissolved therein. Phosphorus oxybromide (25 g) dissolved in dichloroethane (10 mL) was added dropwise thereto at a temperature of not higher than 40° C. The resulting mixture was concentrated under reduced pressure and the residue thus obtained was stirred at 90 to 110° C. for 3 hours. The reaction mixture at the same temperature was added dropwise to THF (250 mL) at a temperature of not higher than 30° C. and the mixture was stirred at room temperature for 30 minutes. A precipitated solid was collected by filtration, washed with THF (100 mL) and dried under reduced pressure to obtain a solid (10.6 g). The solid (0.5 g) thus obtained was dissolved in acetonitrile (30 mL) and active charcoal (0.25 g) was added thereto. Insoluble materials were filtered off and the filtrate was concentrated under reduced pressure to obtain a residue (0.47 g). The residue (0.1 g) thus obtained was placed in a 100 mL Schlenk tube, and the tube was filled with HBr gas and allowed to stand overnight. HBr gas was removed with a diaphragm pump to obtain the title compound (0.13 g).

$^1$H-NMR (300 MHz, DMSO-$d_6$): δ 2.43 (s, 6H), 3.28 (s, 6H), 7.30-7.35 (m, 2H), 7.41-7.65 (m, 3H), 8.10 (s, 2H), 9.06 (brs, 4H).

EXAMPLE 3

Synthesis of N-(3-formylquinolin-7-yl)acetamide

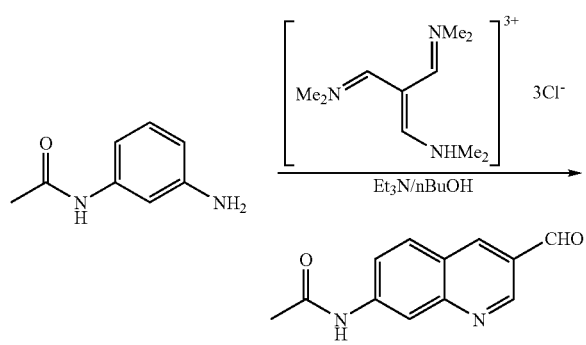

Triethylamine (1.52 g), N-(3-aminophenyl)acetamide (0.50 g) and n-butanol (2 mL) were added to a suspension of 3-(dimethylimino)-2-[(dimethylimino)methyl]-N,N-dimethyl-1-propene-1-aminium trichloride (1.45 g) in n-butanol (8 mL) at room temperature and were dissolved therein. The resulting solution was heated to 80° C., stirred for 3 hours and then cooled to room temperature. After addition of water (1 mL) to the reaction mixture, the solvent was distilled off under reduced pressure. The residue thus obtained was dissolved by addition of acetic acid (2 mL) and water (10 mL) and, again, the solvent was distilled off under reduced pressure. The resulting residue was dissolved by addition of water (10 mL) and the solution was adjusted to pH 8 with sodium hydrogen carbonate. After stirred at room temperature for 1 hour, precipitated crystals were collected by filtration and washed with water (10 mL). The crystals were dried under reduced pressure to obtain the title compound (0.63 g) as pale yellow crystals. Yield: 89%.

$^1$H-NMR (300 MHz, DMSO-$d_6$): δ 2.16 (s, 3H), 7.81 (dd, 1H), 8.14 (d, 1H), 8.52 (d, 1H), 8.83 (d, 1H), 9.21 (d, 1H), 10.18 (s, 1H), 10.52 (s, 1H).

EXAMPLE 4

Preparation of Acetic Acid Solution of Vinamidinium Salt

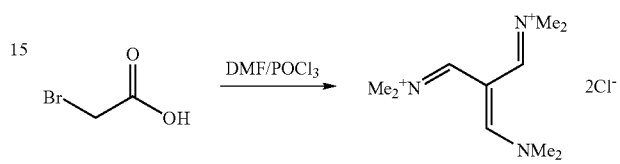

Bromoacetic acid (40.0 g, 288 mmol) was dissolved in dimethylformamide (126 g, 1.73 mol). Phosphorus oxychloride (177 g, 1.15 mol) was added dropwise thereto at a temperature of −5 to 10° C., and the mixture was stirred at 75° C. for 1 hour, then at 95° C. for 1 hour and further at 105° C. for 1 hour. Ethanol (160 mL) was added dropwise thereto at 20 to 30° C. and then tetrahydrofuran (800 mL) was added dropwise thereto at 20 to 30° C., followed by stirring at 20 to 30° C. for 2 hours. Precipitated crystals were filtered off, washed with ethanol/tetrahydrofuran (40 mL/200 mL), and then dried by aeration. The crystals thus obtained were dissolved in acetic acid (320 g). Additional acetic acid (175 g) was added to prepare a 10 w/w % acetic acid solution.

EXAMPLE 5

Synthesis of N-(3-formylquinolin-7-yl)acetamide

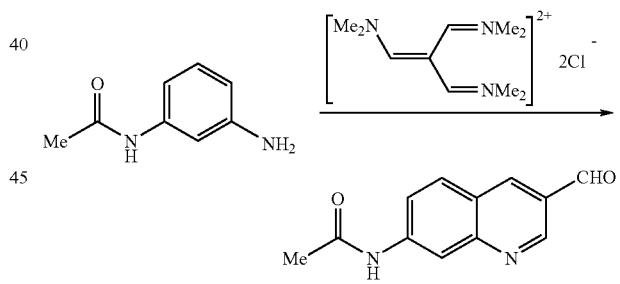

To a 6 w/w % acetic acid solution of 2-dimethylaminomethylene-1,3-bis(dimethyliminio)propane dichloride (3.2 mL, 0.75 mmol) was added N-(3-aminophenyl)acetamide (75 mg, 0.5 mmol). The mixture was refluxed at an external bath temperature of 140° C. for 2.5 hours, and the reaction mixture was cooled to room temperature and concentrated under reduced pressure. Water (3.2 mL) was added to the concentrated residue and the resulting mixture was stirred at room temperature for 1 hour. Precipitated crystals were collected by filtration, washed three times with water (1 mL) and dried under reduced pressure to obtain N-(3-formylquinolin-7-yl)acetamide (93 mg, yield: 86.9%) as white crystals.

$^1$H-NMR (300 MHz, DMSO-$d_6$): δ 2.16 (s, 3H), 7.81 (dd, 1H), 8.14 (d, 1H), 8.52 (d, 1H), 8.83 (d, 1H), 9.21 (d, 1H), 10.18 (s, 1H), 10.52 (s, 1H).

Elemental analysis: $C_{12}H_{10}N_2O_2 \cdot 1H_2O$
Found: C, 62.05; H, 5.11; N, 12.02.
Calcd: C, 62.06; H, 5.21; N, 12.06.

COMPARATIVE EXAMPLE 1

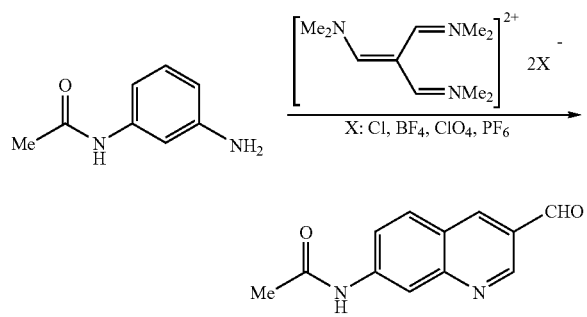

According to the same manner as that described in Example 4, N-(3-aminophenyl)acetamide was used as the substrate and reacted with an acetic acid solution of each kind of vinamidinium salts (Cl salt, $BF_4$ salt, $ClO_4$ salt and $PF_6$ salt). After 2 hours, the formation rate of N-(3-formylquinolin-7-yl)acetamide was measured by HPLC (ODS column; mobile phase: phosphate buffer/acetonitrile=8/2); flow rate: 1 mL/min.; UV 254 nm). The results are as follows.

Formation rate (HPLC area %) in $PF_6$ salt: 41.4%
Formation rate (HPLC area %) in $BF_4$ salt: 63.2%
Formation rate (HPLC area %) in $ClO_4$ salt: 66.0%
Formation rate (HPLC area %) in Cl salt: 84.4%

As seen from the above results of the measurement, the vinamidinium salt having halogen atoms as the anions has the very high reaction selectivity as compared with the other vinamidinium salts, and hence it is a useful starting material as the industrial synthesis of the nitorgen-containing heteroaromatic ring.

EXAMPLE 6

Synthesis of 4-(cyclopropylmethoxy)-N-[3-formyl-8-methylquinolin-7-yl]benzoic acid amide Momorpholine (8.84 g), N-(3-amino-2-methylphenyl)-4-(cyclopropylmethoxy)acetic acid amide (5.00 g) and n-butanol (25 mL) were added to a suspension of 3-(dimethylimino)-2-[(dimethylimino)methyl]-N,N-dimethyl-1-propene-1-aminium trihalide (8.59 g) in n-butanol (50 mL) at room temperature and dissolved therein. The resulting solution was heated to 80° C. and stirred for 4 hours. Acetic acid (12.5 mL) and water (12.5 mL) were added thereto at the same temperature and the mixture was stirred for 30 minutes, followed by cooling to room temperature. After stirring at room temperature for 1 hour, precipitated crystals were collected by filtration and washed in turn with a mixture of acetic acid (25 mL) and water (25 mL), and water (25 mL). The crystals were dried under reduced pressure to obtain the title compound (5.60 g) as white crystals. Yield: 92%.

$^1$H-NMR (300 MHz, DMSO-$d_6$): δ 0.34-0.39 (m, 2H), 0.57-0.63 (m, 2H), 1.24-1.29 (m, 1H), 2.69 (s, 3H), 3.93 (d, 2H), 7.08 (d, 2H), 7.82 (d, 1H), 8.01-8.07 (m, 3H), 8.92 (d, 1H), 9.31 (d, 1H), 10.14 (s, 1H), 10.26 (s, 1H).

INDUSTRIAL APPLICABILITY

The vinamidinium salt having halogen anions of the present invention whose valency number has not been known heretofore in the prior art can be produced in a larger scale because the salt is excellent in reaction selectivity, and free from glass corrosiveness, and can be produced cheaply, and further the salt is excellent in storage stability because of its improved hygroscopicity. Further, an acetic acid solution of the vinamidinium salt having halogen anions is also excellent in storage stability and reaction selectivity, and has superior properties as compared with $BF_4^-$ salt and $PF_6^-$ salt. Therefore, according to the present invention, it is possible to provide the stable vinamidinium salt having the above properties which can be used as a universal reagent useful for synthesizing various substituted nitrogen-containing heteroaromatic rings, its crystals and acetic acid solution, and a method for constructing nitrogen-containing heteroaromatic rings such as quinoline skeleton using them.

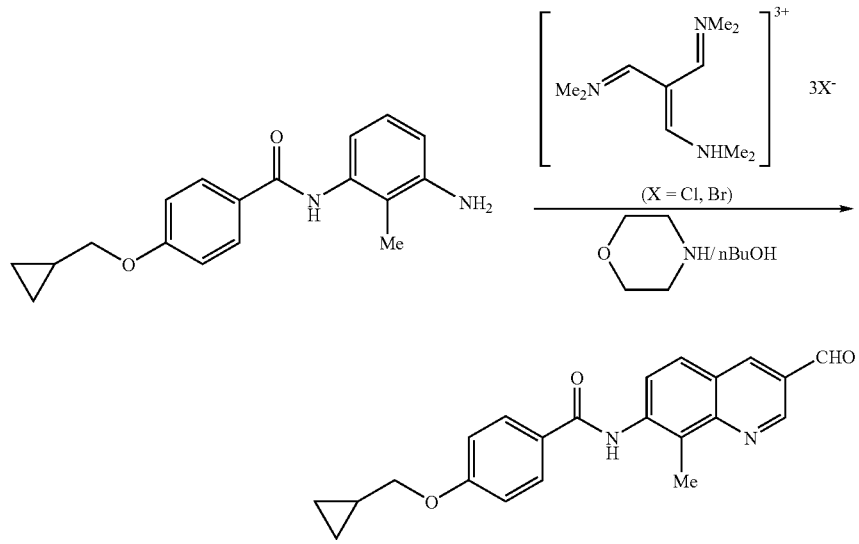

The invention claimed is:

1. A compound represented by the formula (I):

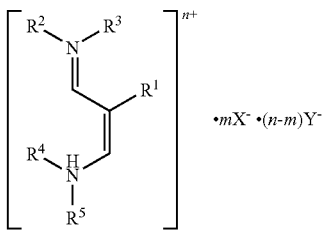

$$\left[ \begin{array}{c} R^2\diagdown N\diagup R^3 \\ \parallel \\ R^1 \\ R^4\diagdown N\diagup H \\ \mid \\ R^5 \end{array} \right]^{n+} \cdot mX^- \cdot (n-m)Y^- \quad (I)$$

wherein $R^1$ represents a hydrogen atom, a halogen atom, a nitro group, a nitroso group, a cyano group, an optionally substituted hydrocarbon group, an optionally substituted heterocyclic group, an optionally substituted hydroxy group, an optionally substituted amino group, an optionally substituted mercapto group, an optionally substituted acyl group, an optionally substituted carbamoyl group, or an optionally substituted sulfonyl group;

$R^2$ and $R^3$ are the same or different and each represents a lower alkyl group, or $R^2$ and $R^3$ may combine together to form a ring;

$R^4$ and $R^5$ are the same or different and each represents a lower alkyl group, or $R^4$ and $R^5$ may combine together to form a ring;

X and Y are the same or different and each represents a bromine atom or a chlorine atom;

n represents a number of 2 or more; and m represents 0 to n.

2. The compound according to claim 1, wherein $R^1$ is a halogen atom, a lower alkyl group substituted by N,N-di(lower alkyl)-imino group, or a $C_1$-$C_6$ aryl group.

3. The compound according to claim 1, wherein $R^1$ is a lower alkyl group substituted by di(lower alkyl)-imino group.

4. The compound according to claim 1, wherein $R^1$ is a dimethyliminomethyl group.

5. The compound according to claim 1, wherein $R^1$ is a dimethyliminomethyl group, each of $R^2$, $R^3$, $R^4$, and $R^5$ is a methyl group and n is 3.

6. The compound according to claim 1, which is isolated.

7. The compound according to claim 1, which is in a solid state.

8. The compound according to claim 1, which is a crystalline compound.

9. An acetic acid solution of the compound according to claim 1.

10. An acetic acid solution of a compound represented by the formula (I'):

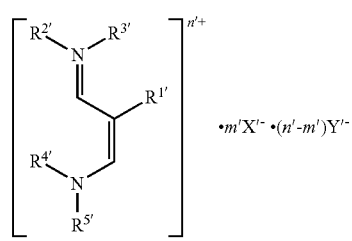

$$\left[ \begin{array}{c} R^{2'}\diagdown N\diagup R^{3'} \\ \parallel \\ R^{1'} \\ R^{4'}\diagdown N \\ \mid \\ R^{5'} \end{array} \right]^{n'+} \cdot m'X'^- \cdot (n'-m')Y'^- \quad (I')$$

wherein $R^{1'}$ represents a hydrogen atom, a halogen atom, a nitro group, a nitroso group, a cyano group, an optionally substituted hydrocarbon group, an optionally substituted heterocyclic group, an optionally substituted hydroxy group, an optionally substituted amino group, an optionally substituted mercapto group, an optionally substituted acyl group, an optionally substituted carbamoyl group, or an optionally substituted sulfonyl group;

$R^{2'}$ and $R^{3'}$ are the same or different and each represents a lower alkyl group, or $R^{2'}$ and $R^{3'}$ may combine together to form a ring;

$R^{4'}$ and $R^{5'}$ are the same or different and each represents a lower alkyl group, or $R^{4'}$ and $R^{5'}$ may combine together to form a ring;

$X'^-$ and $Y'^-$ are the same or different and each represents an anion;

n' represents a number of 1 or more; and m' represents 0 to n'.

11. The acetic acid solution according to claim 10, wherein X' and Y' are the same or different and each represents a bromine atom or a chlorine atom.

* * * * *